(12) United States Patent
Clark et al.

(10) Patent No.: US 9,593,326 B2
(45) Date of Patent: Mar. 14, 2017

(54) PROTEIN VARIANT GENERATION BY REGION SHUFFLING

(75) Inventors: Louis Clark, Redwood City, CA (US); Trish Choudhary, Redwood City, CA (US)

(73) Assignee: Codexis, Inc., Redwood City, CA (US)

(*) Notice: Subject to any disclaimer, the term of this patent is extended or adjusted under 35 U.S.C. 154(b) by 274 days.

(21) Appl. No.: 13/577,651

(22) PCT Filed: Jun. 25, 2012

(86) PCT No.: PCT/US2012/044070
§ 371 (c)(1),
(2), (4) Date: Aug. 7, 2012

(87) PCT Pub. No.: WO2013/003290
PCT Pub. Date: Jan. 3, 2013

(65) Prior Publication Data
US 2014/0005057 A1 Jan. 2, 2014
US 2016/0319273 A9 Nov. 3, 2016

Related U.S. Application Data

(63) Continuation-in-part of application No. 12/884,791, filed on Sep. 17, 2010, now abandoned.

(60) Provisional application No. 61/502,215, filed on Jun. 28, 2011, provisional application No. 61/283,877, filed on Dec. 9, 2009.

(51) Int. Cl.
| | |
|---|---|
| *C12N 15/10* | (2006.01) |
| *C12N 9/02* | (2006.01) |
| *C12P 19/34* | (2006.01) |
| *C12N 9/42* | (2006.01) |
| *C12N 9/24* | (2006.01) |

(52) U.S. Cl.
CPC ....... *C12N 15/1034* (2013.01); *C12N 9/0004* (2013.01); *C12N 9/24* (2013.01); *C12N 9/2434* (2013.01); *C12N 15/1027* (2013.01); *C12P 19/34* (2013.01)

(58) Field of Classification Search
None
See application file for complete search history.

(56) References Cited

U.S. PATENT DOCUMENTS

| | | | |
|---|---|---|---|
| 6,165,793 A | 12/2000 | Stemmer | |
| 2002/0151019 A1* | 10/2002 | Shanklin | C12N 15/8247 435/190 |
| 2010/0093560 A1 | 4/2010 | Colbeck et al. | |
| 2010/0184627 A1 | 7/2010 | Crameri et al. | |
| 2011/0082055 A1* | 4/2011 | Fox et al. | 506/17 |

FOREIGN PATENT DOCUMENTS

| | | |
|---|---|---|
| WO | 9832845 | 7/1998 |
| WO | WO 2013/003290 | 1/2013 |

OTHER PUBLICATIONS

Kirchhoff et al (1993 Genome Research 2:301-4).*
Crameri, A. et al., "Construction and evolution of antibody-phage libraries by DNA shuffling," Nat Med. 1996 vol. 2 No. 1 pp. 100-102.
Kobayashi, N. et al., "Two-step in vitro antibody affinity maturation enables estradiol-17beta assays with more than 10-fold higher sensitivity," Anal. Chem. 2010 vol. 82 No. 3 pp. 1027-1038.
Stemmer, W.P.C., "Rapid evolution of a protein in vitro by DNA shuffling," Nature 1994 vol. 370 pp. 389-391.
Crameri, A. et al., "DNA shuffling of a family of genes from diverse species accelerates directed evolution," Nature 1998 vol. 391 pp. 288-291.
Hamamatsu, Norio et al., "Directed evolution by accumulating tailored mutations: Thermostabilization of lactate oxidase with less trade-off with catalytic activity," Protein Engineering, Design & Selection, vol. 19 No. 11 pp. 483-489, Sep. 2, 2006.
Hamamatsu, Norio et al., "Modified substrate specificity of pyrroloquinoline quinone glucose dehydrogenase by biased mutation assembling with optimized amino acid substitution," Appl Microbiol Biotechnol (2006) 73:607-617, Aug. 31, 2006.
Hamamatsu, Norio et al., "Biased mutation-assembling: an efficient method for rapid directed evolution through simultaneous mutation accumulation," Protein Engineering, Design & Selection vol. 18 No. 6 pp. 265-271, May 31, 2005.
Wong, Tuck Seng et al., "Steering directed protein evolution: strategies to manage combinatorial complexity of mutant libraries," Environmental Microbiology (2007) 9(11), 2645-2659, Jul. 3, 2007.
PCT International Search Report and Written Opinion, dated Jul. 31, 2012, issued in PCT/US2012/044070.
PCT International Preliminary Report on Patentability, dated Jan. 16, 2014, issued in PCT/US2012/044070.
European Extended Search Report dated Jan. 28, 2015 issued in EP 12 80 3889.
Fukuda et al. (2005) "Biased mutagenesis in the N-terminal region by degenerate oligonucleotide gene shuffling enhances secretory expression of barley α-amylase 2 in yeast," Protein Engineering, Design & Selection, 18(11):515-526.
Kolkman et al., (May 1, 2001) "Directed evolution of proteins by exon shuffling," Nature Biotechnology, 19:423-428.
O'Maille et al.,(2002) "Structure-based Combinatorial Protein Engineering (SCOPE)," Journal of Molecular Biology, 321(4):677-691.
European Office Action dated Aug. 2, 2016 issued in EP 12 803 889.0.

* cited by examiner

*Primary Examiner* — Christopher M Gross
(74) *Attorney, Agent, or Firm* — Weaver Austin Villeneuve & Sampson LLP

(57) ABSTRACT

Region shuffling methods for efficiently introducing diversity and exploring sequence space are described. Libraries produced directly from these methods contain high fractions of protein variants harboring multiple beneficial mutations. Typically, the methods produce these variants efficiently without the need for sequencing beneficial mutants identified at intermediate stages of the process.

38 Claims, 12 Drawing Sheets

Pool A

Region 1

Pool B

Region 2

Pool C

Region 3

Sub-library A

| (1a) X | (2) | (3) | X (1b) | (4) |

| X (1a) | (2) | (3) | (1b) X | (4) |

Amplification using two primer sets
(one for sub-region 1a and another
for sub-region 1b)

Pool A (isolates)

Intra-Region Shuffling

1) Protein is divided into Regions (by structure, or just linear)

2) Mutations are grouped and screened according to designated Regions

3) "Hits" from each region are pooled for plasmid extraction

Intra-Region Shuffling

5) Uracil N-glycosylase and Endonuclease IV are used to fragment the regions by excision of uracil bases and phosphodiester bond cleavage at these sites, respectively.

6) Fragmented regions are used as template in a SOE PCR to create full length combinatorial library

PROTEIN VARIANT GENERATION BY REGION SHUFFLING

CROSS-REFERENCE TO RELATED APPLICATIONS

This application is a 371 National Phase application of PCT/US2012/044070 under 35 U.S.C. §371, filed on Jun. 25, 2012, which claims benefit under 35 U.S.C. §119(e) to U.S. Provisional Patent Application No. 61/502,215, entitled: PROTEIN VARIANT GENERATION BY REGION SHUFFLING, filed 28 Jun. 2011; this application also claims priority under 35 U.S.C. §120 as a continuation-in-part to U.S. patent application Ser. No. 12/884,791, filed on Sep. 17, 2010, which claims the benefit under 35 U.S.C. §119(e) to U.S. Provisional Application No. 61/283,877, filed on Dec. 9, 2009; which is the above applications are herein incorporated by reference in its their entirety for all purposes.

BACKGROUND

Various methods are used to identify polypeptides having desired activities such as therapeutic effects, the ability to produce useful compositions from feed stocks, etc. Directed evolution and other protein engineering technologies can be used to discover or enhance the activity of polypeptides of commercial interest. For example, if the activity of a known enzyme is insufficient for a commercial process, directed evolution may be used to improve the enzyme's activity on a substrate of interest. Current methods are often limited by the time and cost required to identify useful polypeptides. In some instances, it may take months or years, at great expense, to find a new polypeptide with the desired activity, if one is ever found. Part of the problem arises from the great number of polypeptide variants that must be screened. Thus, there is a need for improved methods and libraries that identify novel polypeptide variants having a desired activity.

SUMMARY

Various methods for efficiently introducing diversity and exploring sequence space are described here. Libraries produced directly from these methods contain high fractions of protein variants harboring multiple beneficial mutations. The methods produce these variants efficiently without the need for sequencing beneficial mutants identified at intermediate stages of the process.

In one aspect, this disclosure pertains to methods of introducing diversity into a reference protein sequence. Such methods may be characterized by the following operations: (a) selecting a plurality of mutant proteins having sequences that vary from the reference protein sequence; (b) isolating a first group of nucleic acid segments, each nucleic acid segment in the first group encoding a first region of the reference protein sequence but not encoding substantially any other region of the reference protein sequence, and each nucleic acid segment in the first group encoding its own distinct mutation, which mutation is found in a mutant protein selected in (a); (c) isolating a second group of nucleic acid segments, each nucleic acid segment in the second group encoding a second region of the reference protein sequence but not encoding substantially any of the first region of the reference protein sequence, and each nucleic acid segment in the second group encoding its own distinct mutation, which mutation is found in a mutant protein selected in (a); and (d) assembling at least the isolated nucleic acid segments from (b) and (c) into full length nucleic acid sequences encoding new mutant proteins. Operation (b) may be performed without determining sequences of members of the first group of nucleic acid segments. Further, in some embodiments, operations (b)-(d) are performed without determining sequences of the mutant protein sequences.

In some cases, the reference protein sequence is a wild type protein sequence. The plurality of mutant proteins may be produced by various processes. In one example, they are produced by introducing point mutations into the reference protein sequence. For example, the mutant proteins may be produced by performing saturation mutagenesis on the reference protein sequence. In various implementations, the plurality of mutant proteins contains, collectively, at least about 100 mutations.

In one embodiment, the selection in (a) involves identifying mutant proteins having potentially beneficial mutations across the protein sequence. Typically, the process includes an operation of grouping individual mutant proteins from the plurality of mutant proteins selected in (a) based on regions of the reference protein or peptide sequence where mutations occur. This produces the first and second groups. Frequently, the first and second groups each contain multiple nucleic acid segments harboring diverse mutations. In some examples, the first group of nucleic acid segments contains at least about 2 distinct, at least about 5 distinct, at least about 8 distinct, at least about 10 distinct, at least about 15 distinct, at least about 20 distinct or more nucleic acid segments, each having a distinct sequence.

In certain embodiments, isolating the first group of nucleic acid segments involves amplifying the nucleic acid segments in the first group in a single amplification reaction. In some embodiments, the amplifying is performed under conditions that do not substantially amplify nucleic acid segments encoding any regions other than the first region. In some embodiments, isolating the second group of nucleic acid segments involves amplifying the nucleic acid segments in the second group in a single second amplification reaction. In some embodiments, the process of isolating the first group of nucleic acid segments is performed without first identifying any mutation contained in the first group of nucleic acid segments. In various embodiments, the first group of nucleic acid segments contains at least about 5 distinct nucleic acid segment sequences.

In further embodiments, the methods include an operation of isolating a third group of nucleic acid segments, with each nucleic acid segment in the third group encoding a third region of the reference protein sequence but not encoding substantially any of the first or second regions of the reference protein sequence. Further, each nucleic acid segment in the third group normally encodes its own distinct mutation, which mutation is found in a mutant protein selected in (a). Additional groups of nucleic acid segments encoding additional regions of the reference protein sequence may be included in the methods.

In certain embodiments, the assembling in (d) is performed using an overlap extension Polymerase Chain Reaction. In certain embodiments, the assembling in (d) is performed without using primers. In one example, the assembling in (d) is performed using homologous recombination in yeast. Often recombinant proteins produced by the full length nucleic acid sequence in (d) are evaluated for a beneficial property.

In some embodiments, the nucleic acid segments from (b) used to assemble the full length nucleic acid sequences in (d) are present in non-equimolar amounts during the assembling. The particular isolated segments present in non-equimolar amounts may be chosen based on one or more properties of the associated mutant proteins harboring mutations encoded by the isolated segments present in non-equimolar amounts.

Another aspect of the disclosure pertains to methods of introducing diversity that may be characterized by the following operations: (a) selecting a plurality of mutant proteins derived from a reference protein sequence; (b) amplifying a first group of nucleic acid segments in a single amplification reaction, with each such nucleic acid segment in the first group encoding a first region of the reference protein sequence, but not encoding substantially any other region of the reference protein sequence, and each nucleic acid segment in the first group encoding its own distinct mutation, which mutation is found in a mutant protein selected in (a); (c) amplifying a second group of nucleic acid segments in a second amplification reaction, with each nucleic acid segment in the second group encoding a second region of the reference protein sequence, but not encoding substantially any of the first region of the reference protein sequence, and each nucleic acid segment in the second group encoding its own distinct mutation, which mutation is found in a mutant protein selected in (a); and (d) assembling at least the isolated nucleic acid segments from (b) and (c) into full length nucleic acid sequences encoding new mutant proteins. Further, the embodiments may include repeating operation (c) for a third, fourth, fifth, sixth or more group of nucleic acid segments encoding a third region, a fourth region, a fifth region, a sixth region or more regions of the reference protein sequence. In some embodiments, the repetitions of operation (c) may be performed sequentially and in other embodiments the repetitions of operation (c) may be performed simultaneously.

In some embodiments, the methods include pooling the nucleic acid segments in the first group prior to operation (b). The pooling may involve mixing at least about 10 distinct nucleic acid segment sequences from the first group. In some embodiments, the operation of amplifying the first group of nucleic acid segments is performed using a single set of primers.

Yet another aspect of the disclosure pertains to introducing diversity via methods characterized by the following operations: (a) screening a first sub-library having mutations in a first region of a reference protein sequence to provide a first selected group of mutants; (b) screening a second sub-library having mutations in a second region of the reference protein sequence to provide a second selected group of mutants; (c) isolating first nucleic acid sequences encoding the first region of the first selected group of mutants; (d) isolating second nucleic acid sequences encoding the second region of the second selected group of mutants; and (e) producing full length nucleic acid sequences by randomly joining the first nucleic acid sequences and the second nucleic acid sequences.

In some embodiments, methods of introducing diversity include intra-region shuffling. Such methods may be characterized by the following operations: (a) selecting a plurality of mutant proteins derived from a reference protein sequence; (b) amplifying a first group of nucleic acid segments, wherein each nucleic acid segment in the first group encodes a first region of the reference protein sequence, but does not encode substantially any other region of the reference protein sequence, and each nucleic acid segment in the first group encodes its own distinct mutation, which mutation is found in a mutant protein selected in (a); (c) fragmenting and optionally recombining the amplified nucleic acids produced in (b) to thereby produce a pool of nucleic acids encoding the first region and having increased diversity; (d) amplifying a second group of nucleic acid segments, wherein each nucleic acid segment in the second group encodes a second region of the reference protein sequence, but does not encode substantially any of the first region of the reference protein sequence, and each nucleic acid segment in the second group encodes its own distinct mutation, which mutation is found in a mutant protein selected in (a); and (e) assembling at least the isolated nucleic acid segments from (c) and (d) into full length nucleic acid sequences encoding new mutant proteins.

These and other features and advantages will be described in further detail below with reference to the associated drawings.

DETAILED DESCRIPTION

I. Introduction

Figure 1:
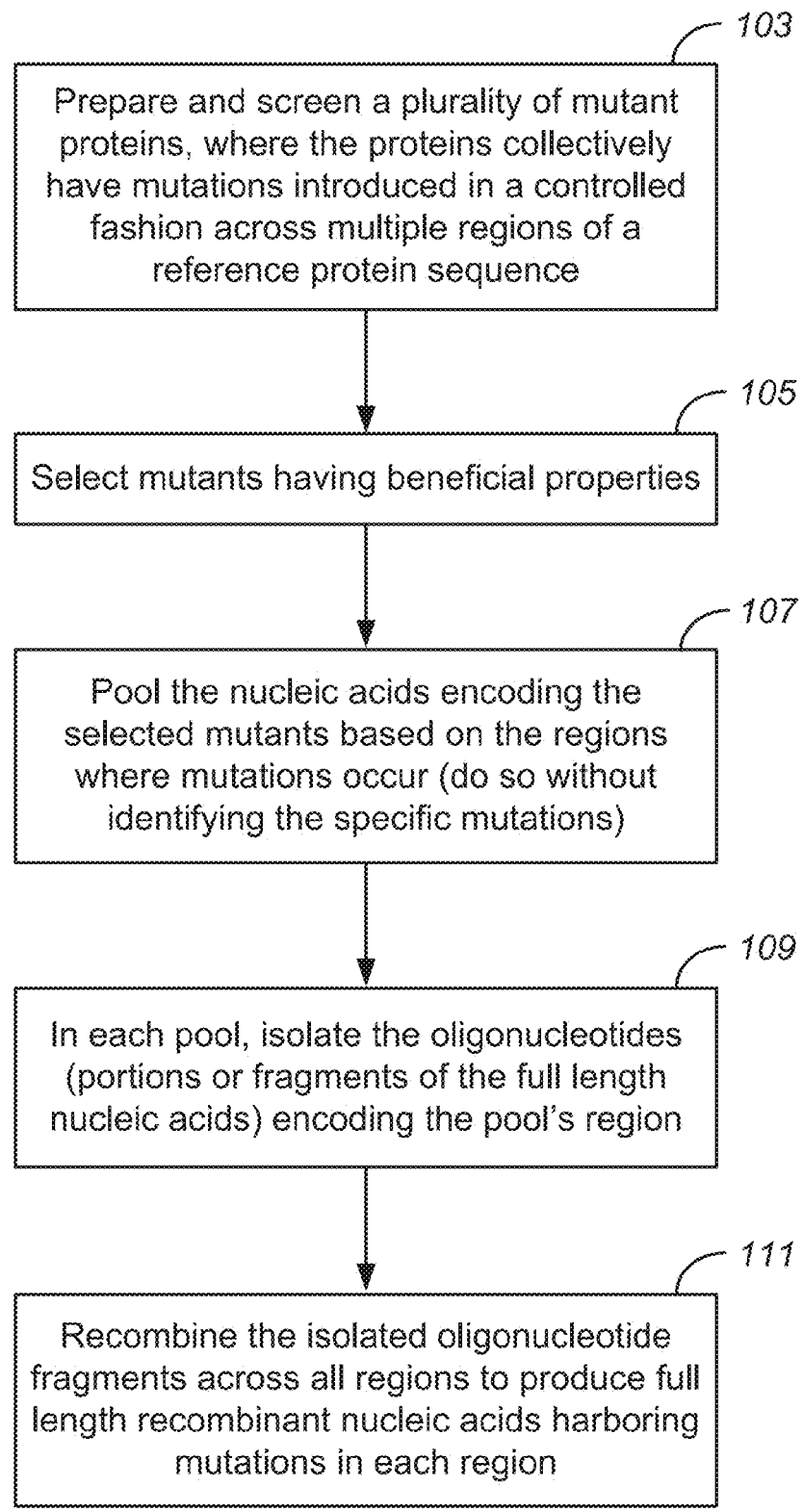
FIG. 1 is a process flow chart depicting a sequence of techniques employed in some embodiments of region shuffling.

Certain methods disclosed herein, which are sometimes generally referred to as "region shuffling," provide a way to efficiently identify proteins having controlled diversity (mutation sites) across the sequence of a parent or "reference" protein. The disclosed methods may be used at any stage in a directed evolution project. In some embodiments, they will be used at relatively early stages, particularly in early rounds of such a project.

Among the benefits that may be realized using region shuffling methods of the invention are (i) producing derivative variants without sequencing the individual mutations that feed into the region shuffling (typically those mutations found in multiple parental variants), and (ii) promoting creation of derivative variants having mutations in each of the two or more regions of the variant sequences. The first of these benefits greatly speeds the exploration of sequence space. The second biases the exploration toward multi-mutation variants. Overall, region shuffling rapidly generates combinatorial libraries employing the full range diversity from an initial screen library; e.g., a screen library based on many possible individual mutations.

To facilitate understanding of the invention, a high level description of certain embodiments of region shuffling processes are presented. In some embodiments, region shuffling employs a rational designation of the regions making up a parent or reference protein before any variants are created or screened. In certain embodiments, the region shuffling method is designed so that introduced mutations span a significant fraction of the protein's length, over multiple regions; in some cases over the protein's entire length. In some preferred embodiments, one may conduct saturation mutagenesis to produce a point mutation at each and every amino acid in the protein. Alternatively, point mutations at fewer than each and every amino acid position can be employed. In some embodiments, point mutations can be made at specifically selected amino acid positions.

Regardless of the nature and origin of the set of mutations, the resulting mutants are characterized for example, for activity, stability, or other phenotypic property. These phenotypic properties are determined by screening whole proteins (variants) that carry the mutations. Proteins carrying beneficial mutations in each region are identified and the associated mutations are selected for incorporation in new protein variants for production or for subsequent rounds of evolution.

The selected mutants are pooled based on the locations (specifically the regions) of their mutations. For example, mutants having mutations from different regions of the parent protein sequence are grouped so that mutants having mutations from a particular region are included in one sub-library, mutants having mutations from a second region are included in a second sub-library, and so on. Thus, in this embodiment each region of the protein has associated with it multiple beneficial mutations and these beneficial mutations are pooled in region-specific sub-libraries.

The regions of the reference protein sequence can be defined using many different criteria. In one approach, the regions are contiguous groups of amino acids in the reference protein sequence. Alternatively, or in addition, the amino acids in a given region include some that are not contiguous.

In some embodiments, there are more than two regions per protein. For example, there may be about three to ten (e.g., three, four, five, six, seven, eight, nine or ten) regions in a protein, although it is not uncommon for significantly higher numbers of regions to be employed, e.g., about 15 regions, about 20 regions or more.

Generally, the embodiments disclosed herein do not rely on sequencing of beneficial mutants in order to select or locate the underlying beneficial mutations or to place them in a particular pool. To select a mutant for a given pool, all that need be known is which region of the protein the relevant mutation or mutations occur in.

All nucleic acid sequences having mutations mapping to a given region (e.g., mutations bounded within the region) are binned and placed in a pool. In some embodiments, each individual nucleic acid variant in the pool harbors at least one of the beneficial mutations.

Collectively, the nucleic acid sequences harboring the mutations in a given pool are selectively amplified or otherwise isolated. The isolating removes all or nearly all of the nucleic acid sequences lying outside the region associated with the pool. Thus, the resulting isolated nucleic acid sequences contain little or no sequence from regions outside the region associated with the pool under consideration.

In some embodiments, a pool may be weighted or biased toward one or another of the beneficial mutations that were previously identified. In other embodiments, each of the beneficial mutations is equally weighted in the pool, such that sequences containing each mutation are present in equimolar or substantially equimolar concentrations. Biasing toward a particular mutation provides control over the relative contributions of one or more of the mutations in a given region. This in turn controls the relative amounts of particular sequences in the final recombination product, e.g., the library of full-length recombinant genes coding the proteins of interest. The biasing may be accomplished by various techniques. In one embodiment, for example, the nucleic acid sequences seeding an amplification reaction may contain excess amounts of a nucleic acid encoding a mutant observed to be particularly beneficial.

One embodiment for isolating the pooled sequences for a specified region of a nucleic acid involves simultaneously amplifying all the various mutant sequences found within a block of contiguous nucleotides together in a single amplification reaction. In this embodiment, only one set of primers (per region) is required for the pooled amplification reaction.

At the end of the pooling and isolating operations, each of the pools contains only nucleic acids encoding the single region associated with the pool. In some embodiments, each nucleic acid sequence in the pool will harbor one or more putative beneficial mutations. In other embodiments, a fraction of the nucleic acid segments have no beneficial mutations.

The isolated nucleic acids pooled for the separate regions are ultimately spliced together to construct a sequence encoding a full length protein. Because all or nearly all the nucleic acid segments in any pooled region typically harbor at least one mutation, the full length protein resulting from region shuffling often has at least one mutation in most or all of the various regions that make up the full length sequence. In some embodiments, a recombinant protein has at least one mutation in each of the regions. However, this need not always be the case, as some wild type (parental) sequence may be present in some of the region pools. In some cases, this may be due to masking of mutations at the edges the regions during amplification. For example, when the fragments are not adequately staggered (or are otherwise too close to the region boundary), one or more mutations may lie in the area where primers attach to amplify the individual regions and may therefore be masked. If the selection "threshold" is set too low during the selection of parental variants to be included in the hit pool for a given region, then one may see a certain level of "false positives" which are selected due to noise in the assay. For example, choosing all the variants having activity 1.1 fold above the parent activity for a specific screened property (e.g., thermostability) may result in some "noise" or parental background as compared to a selection process that takes forward only the variants identified as having at least 1.5 or higher fold activity over the parent for the specifically screened property. Therefore, without sequencing, one may assume that a number of false positives are carried through when the threshold is set too low.

Various techniques may be employed to splice together the nucleic acid segments from the region pools to form the full length sequence. Some of these non-limiting techniques are PCR-based recombination techniques such as SOE (splicing by overlap extension) and other PCR (polymerase chain reaction). Other techniques may involve organism-based recombination such as yeast homologous recombination techniques.

To address the possibility that some mutations may appear near the edge or boundary of a given region, and thereby be masked by primers used in PCR based recombination, certain embodiments include techniques which employ extended fragments for the recombination technique. In such cases, the fragments used in the recombination contain some terminal nucleotides that are not strictly contained within the boundaries of their associated regions. Thus, for example, the fragment used for recombination may contain the region of interest and one or two additional segments straddling the region, which segments correspond to small portions of adjacent regions. The outer additional sequences are complementary to edge sequences in bounding regions of the reference sequence.

II. Definitions

The following discussion is provided as an aid in understanding certain aspects and advantages of the disclosed embodiments.

The terms "protein," "polypeptide" and "peptide" are used interchangeably to denote a polymer of at least two amino acids covalently linked by an amide bond, regardless of length or post-translational modification (e.g., glycosylation, phosphorylation, lipidation, myristilation, ubiquitination, etc). The terms include compositions conventionally considered to be fragments of full length proteins or peptides. Included within this definition are D- and L-amino acids, and mixtures of D- and L-amino acids. The polypeptides described herein are not restricted to the genetically encoded amino acids. Indeed, in addition to the genetically encoded amino acids, the polypeptides described herein may be made up of, either in whole or in part, naturally-occurring and/or synthetic non-encoded amino acids. In some embodiments, a polypeptide is a portion of the full length ancestral or parental polypeptide, containing amino acid additions or deletions (e.g., gaps) or substitutions as compared to the amino acid sequence of the full length parental polypeptide, while still retaining functional activity (e.g., catalytic activity).

"Native sequence" or "wild type sequence" as used herein refers to a polynucleotide or polypeptide isolated from a naturally occurring source. Included within "native sequence" are recombinant forms of a native polypeptide or polynucleotide which have a sequence identical to the native form.

"Recombinant" refers to a polynucleotide synthesized or otherwise manipulated in vitro or in vivo (e.g., "recombinant polynucleotide"), to methods of using recombinant polynucleotides to produce gene products in cells or other biological systems, or to a polypeptide ("recombinant protein") encoded by a recombinant polynucleotide.

"Host cell" or "recombinant host cell" refers to a cell that includes a recombinant nucleic acid molecule. Thus, for example, recombinant host cells can express genes that are not found within the native (non-recombinant) form of the cell.

"Mutant" or "variant" as used herein refers to an amino acid or polynucleotide sequence (and the nucleic acid sequences encoding them) which has been altered by substitution, insertion, cross-over, deletion, and/or other genetic operation. For purposes of the present disclosure, a mutant or variant is not limited to a particular method by which it is generated. In some embodiments, a mutant or variant sequence can have increased, decreased, or substantially similar activities or properties in comparison to the parental sequence. In some embodiments, the polypeptide may contain one or more amino acid residues that have been mutated as compared to the amino acid sequence of the wild type polypeptide. In some embodiments, one or more amino acid residues of the polypeptide are held constant, are invariant, or are not mutated as compared to a parent polypeptide in the variant polypeptides making up the plurality. In some embodiments, the parent polypeptide is used as the basis for generating variants with improved robustness or other properties.

The term "region" refers to one or more subsequences within a protein or nucleotide sequence, but not including the entire protein or nucleotide sequence. Typically, a protein or nucleic acid contains multiple distinct regions. Each region may contain sites for mutations made with respect to a reference sequence. A region typically contains at least one set of contiguous amino acids or nucleotides. In the simplest example, a protein contains two regions, one being defined by the carbon-terminus side of the protein and the other region being defined by the nitrogen-terminus side of the protein. In a different approach to defining regions, the amino acids or nucleotides in a given region are not limited to those that are contiguous with one another, but are related in other ways. For example, a region may be composed of amino acids that are spatially proximate to one another in a folded protein's three-dimensional conformation. In such cases, a region may contain two or more separate blocks of contiguous amino acids. Typically, there will be significantly more than two regions per protein or nucleic acid. For example, there may be about five to ten (e.g., 5, 6, 7, 8, 9 or 10) regions in a protein or nucleic acid. It is not uncommon for significantly higher numbers of regions to be employed, e.g., about 20 regions or more.

The term "isolation" refers to the separation of one region of a nucleotide sequence from other regions of the nucleotide sequence. Isolation is typically performed via an amplification reaction, but this need not be the case. Ultimately a pool of isolated nucleotide sequences is greatly enriched in nucleic acid segments containing only sequences for a particular region of interest. Thus, isolated nucleic acid sequences are shorter than full length sequences encoding an entire protein. Typically an isolated sequence does not encode substantially any other region of the reference protein sequence but the region of its pool. However, certain implementations provide some overlap between sequences of adjacent regions. Specifically some implementations allow sufficient overlap of nucleic acid segments from adjacent regions to permit ligation or recombination by overlap extension PCR, homologous recombination in yeast, or a related technique.

The term "pool" refers to a mixture or other combination of related nucleic acids. In a specific embodiment, the pooled nucleic acids are related in that they each contain mutations in a single region. The pooled nucleic acids may be conveniently processed together in a single reaction, such as an isolation or amplification reaction. The proteins or associated nucleic acids having mutations in a defined region are sometimes referred to collectively as a "sub-library."

"Desired activity" or "beneficial property" means a measurable property exhibited by the polypeptide(s) for which a plurality may be screened. Examples of desired activities can include, but are not limited to, thermostability, pH stability, substrate specificity, chemoselectivity, stereoselectivity, stereoselectivity, enantioselectivity, stereospecificity, enantiospecificity, regioselectivity, ligand specificity, receptor agonism, receptor antagonism, conversion of a cofactor, and product selectivity, or any combination thereof. Mutants may also be screened to identify a polypeptide having improved, enhanced, diversified or expanded activity, such as an increased rate of product formation, an increase in percent conversion of a substrate to a product, acquisition of a new catalytic ability (such as an ability to react with a substrate with which a plurality's parent polypeptide does not react) or an increased affinity of a receptor for a ligand.

"Parental polypeptide," "ancestral polypeptide," "ancestor," or "parent" is generally used to refer to the wild type polypeptide or a variant produced prior to region shuffling and then used in region shuffling. In some embodiments, mutants used in region shuffling are directly related to a parent polypeptide. In some embodiments, the ancestor or parent polypeptide is robust to extremes of temperature, pH and/or solvent conditions and can serve as the basis for generating variants for region shuffling. In some embodiments, the parental polypeptide is not robust to extremes of temperature, pH and/or solvent conditions, and the parental polypeptide is evolved to make a robust parent polypeptide from which variants are generated for region shuffling.

III. Process

FIG. 1 presents a flow chart depicting certain operations that may be performed in accordance with various region shuffling embodiments disclosed herein. The process begins as depicted in block 103 with the preparation and screening of multiple mutant proteins. Typically, these proteins collectively have mutations spread across multiple different regions of a reference protein sequence. Depending upon the technique employed to prepare the mutant proteins, these mutations may be individually identified by the regions in which the mutations are located. For example, one group of mutants may have mutations only in a first region of the reference sequence, while a second group of mutants may have mutations only in a second region of the reference sequence, and so on. In certain embodiments, the first group of mutants is provided in a first sub-library, the second group of mutants is provided a second sub-library, and so on, with each sub-library limited to mutants having mutations in the associated region.

Returning to the process of FIG. 1, some of the mutants prepared and screened in operation 103 are selected for their beneficial properties in an operation 105. The selected mutants may be selected for their improved activity, stability, etc. in comparison to a reference protein or a threshold value. For example, each selected variant may have enhanced reactivity with a substrate as compared to the parent polypeptide.

If the individual mutants prepared in operation 103 are divided into sub-libraries, each sub-library may be separately screened and beneficial mutants may be selected therefrom. In this manner, each of the mutants selected in operation 105 is directly associated with a particular region of the reference sequence and can be processed accordingly.

At some point after screening, the nucleic acids encoding the mutants selected in operation 105 are extracted and further processed. In an operation 107 of the flow chart, the nucleic acids encoding selected mutants are pooled based upon the region where their associated mutations reside. Therefore, there will be one pool of nucleic acids encoding mutants having mutations in a first region, a second pool of nucleic acids encoding the mutants having mutations in a second region, and so on, with a separate pool of nucleic acids for each region of the reference protein sequence. If the original mutant proteins prepared and screened in operation 103 are subdivided into individual sub-libraries, the process of pooling their associated nucleic acids in operation 107 may be relatively simple, as the cells expressing these mutants have been segregated by region from early in the process. Alternatively, the individual mutants or their associated cells may be separately addressed early in the process to reference the particular regions where their mutations occur. This will allow the nucleic acids considered in operation 107 to be appropriately selected and pooled based on their mutation regions.

One benefit of the region shuffling method described herein is that it efficiently produces libraries enriched in beneficial mutations without incurring the time and expense of sequencing the selected mutants or otherwise identifying beneficial mutations (by sequence) prior to pooling the sequences or performing a random recombination of nucleic acid sequences encoding such mutations. Thus, in block 107, the pooling of nucleic acids encoding selected mutants is typically conducted without first identifying the specific mutations. Thus, in various embodiments, all that is known is that all the nucleic acids in the pool encode mutants harboring mutations in the same region of the reference sequence.

After the pools are created in operation 107, the next operation in the process (operation 109) isolates the individual nucleic acid portions that encode the region associated with the pool. Thus, for example, a pool associated with a first region of the sequence will be treated in a manner to isolate the nucleic acid portions that encode only the first region of the sequence. The nucleic acid portions that have been isolated will not, typically, include substantially any sequence outside the region associated with the pool in question. Thus, the isolated nucleic acid sequences encode only a portion of the full-length protein sequence, and that portion is the associated region of the protein sequence. In this manner, the process creates multiple pools of isolated nucleic acid sequences, with each pool encoding a different region of the overall protein sequence. The isolated nucleic acids in these pools can be viewed as building blocks for assembling full-length nucleic acids encoding full-length protein sequences.

Returning to the process flow chart of FIG. 1, the next operation in the depicted process (operation 111) recombines the isolated region-specific nucleic acid fragments across all regions of the reference sequence to produce full-length recombinant nucleic acid sequences harboring mutations in most or all regions. The recombination operation makes use of the individual pools of isolated nucleic acid fragments produced in operation 109. Thus, the recombination makes use of (i) multiple distinct nucleic acid sequences encoding a first region and harboring various mutations in the first region, (ii) multiple distinct nucleic acid sequences encoding a second region and harboring various distinct mutations within the second region, and (iii) so on. The resulting re-assembled full-length nucleic acids will typically have at least one mutation in each of the various regions defined in the initial reference sequence. Further, the resulting recombinant library of full-length nucleic acids will have great diversity in that the various available mutations in each of the regions will be randomly joined.

Figure 2A:
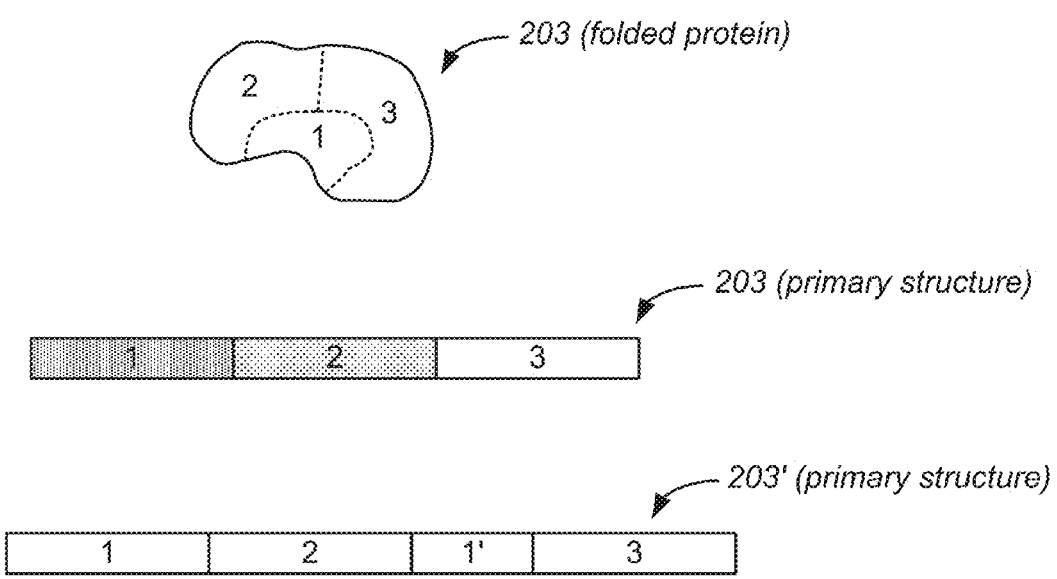
FIGS. 2A-2E are schematic depictions of peptides and nucleic acid sequences at various stages in a region shuffling procedure in accordance with certain embodiments.

One example of the above described process is schematically illustrated in FIGS. 2A through 2E. As shown in FIG. 2A, a protein 203 contains three regions, which are identified by reference numbers 1, 2, and 3. Folded and primary structures of protein 203 are depicted in the top and middle illustrations of FIG. 2A. Any one or more of these regions may be defined by contiguous stretches of amino acids in the protein. Alternatively, any one of the regions may be defined by two or more contiguous sequences that are related in some manner such as by being in close physical proximity to one another in the protein's tertiary structure. An example of a region (region 1) having two separated contiguous sequences is shown in primary structure of a protein 203'. See the bottom illustration of FIG. 2A.

Figure 2B:
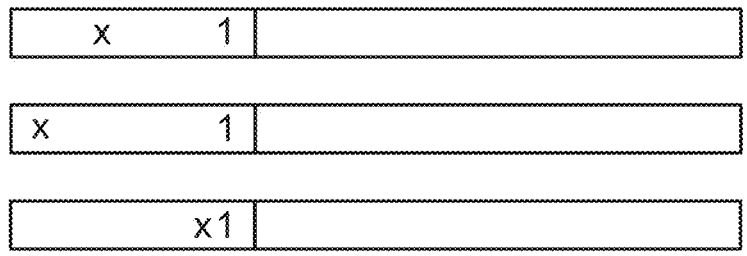
Figure 2B:
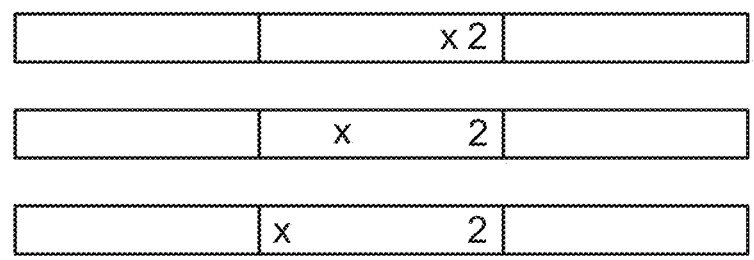
Figure 2B:

FIG. 2B depicts three separate sub-libraries containing variants of the protein 203 from FIG. 2A. Each sub-library is limited to those variants that contain mutations in the particular region associated with the sub-library. Thus, "sub-library A" is limited to variants having mutations in region 1, "sub-library B" is limited to variants having mutations in region 2, and "sub-library C" is limited to variants having mutations in region 3. For convenience, only three variants are shown in each of the sub-libraries. Typically there will be many more than three variants per sub-library. Note also that each variant in a given sub-library contains a distinct mutation, albeit within the same region of the sequence. In some cases, multiple mutations are found at the same position in the sequence. This situation may result, for example, when performing site saturation mutagenesis, which as noted screens all 20 amino acid substitutions at a given position, and sometimes more than one mutation at that position can confer a selective advantage.

Further, note that in FIG. 2B each of the variants shown in each of the sub-libraries is a full-length variant that has not been fragmented or otherwise constrained to the sequences for the separate regions. Additionally, while the sub-libraries are described herein as groups of variant proteins, sub-libraries also refer to the nucleic acids encoding those proteins. From a given host cell expressing a particular mutant protein, the nucleic acid encoding that protein can be extracted and pooled.

Figure 2C:
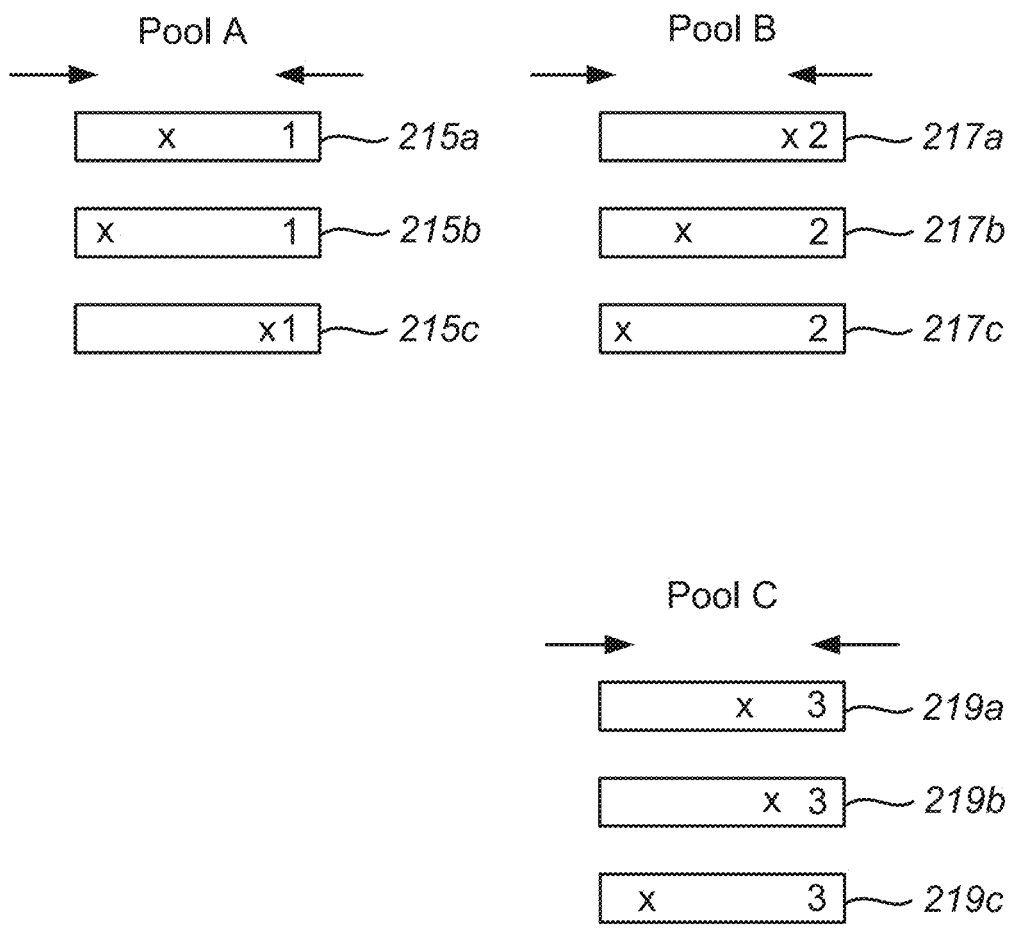

In FIG. 2C, region isolates from the pools are illustrated. The region 1 isolates, shown as 215a, 215b, and 215c, contain only the nucleotides encoding the first region of protein 203. The full-length nucleic acids shown in FIG. 2B are modified to produce the isolates in FIG. 2C by an appropriate process such as selective amplification of the region sequences within the full-length nucleic acids. As shown in FIG. 2C, isolates 217a through 217c are produced for the second region (from pool B) and isolates 219a through 219c are produced for the third region (from pool C).

Figure 2D:
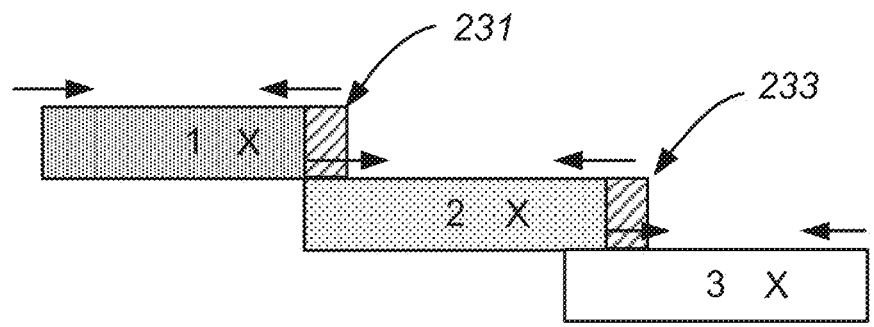
Figure 2E:
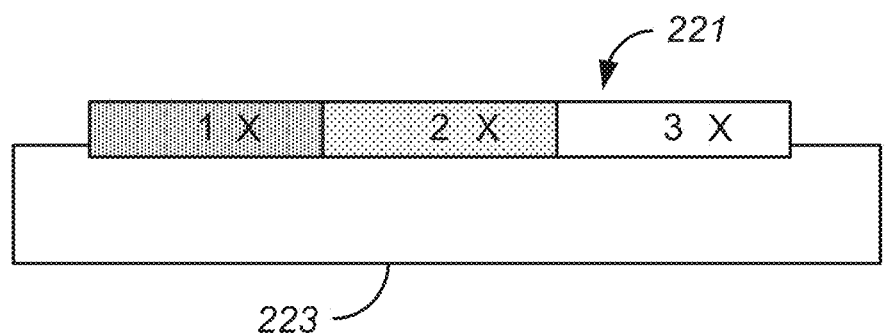
Figure 2F:
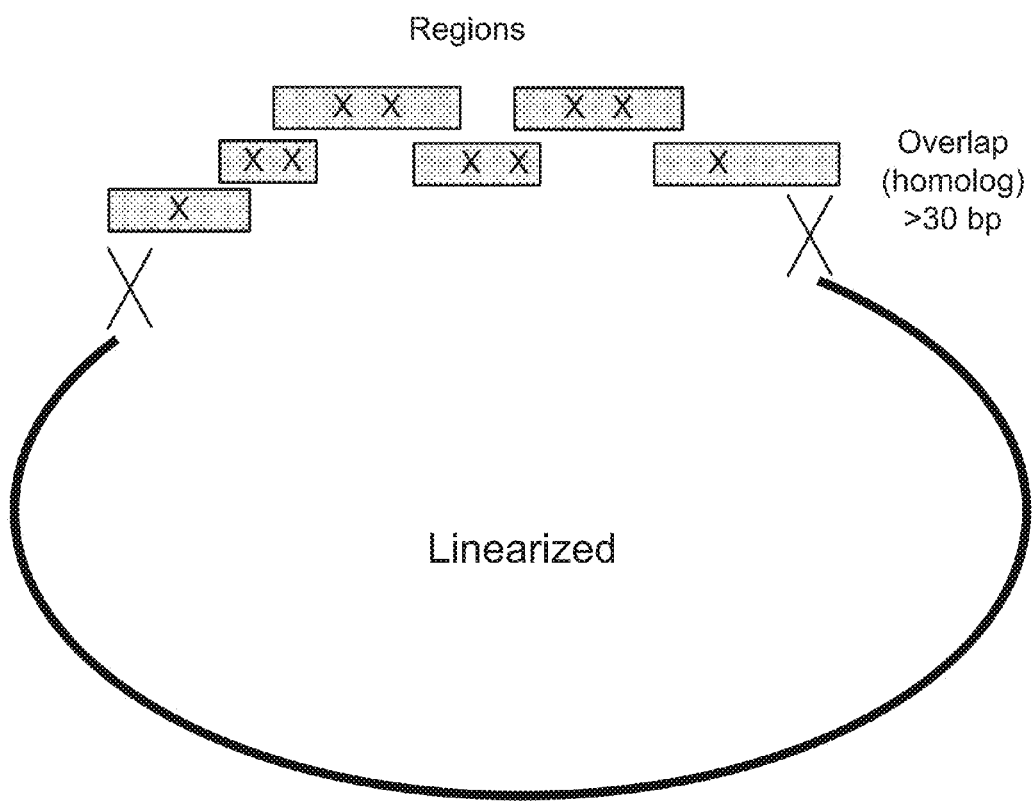
FIG. 2F depicts homologous recombination in yeast as a technique for recombining region isolates into full length sequences.

After creating multiple copies of the isolates in each pool (typically by using PCR amplification), the individual region isolates from various pools are randomly reassembled to form full-length nucleic acids. This recombination can take place by various mechanisms. In one example, the isolated fragments are cloned into an expression vector using homologous recombination in yeast. By this process, the individual isolated fragments are recombined to produce full-length nucleic acids capable of encoding new variant proteins and are cloned into the expression vector by design of sequence overlap. Homologous recombination is an extremely efficient repair process that occurs in yeast to repair harmful breaks that spontaneously occur on both strands of DNA, (double-strand breaks). The process involves the exchange of DNA between two similar strands of DNA based on sequence identity as shown in the diagrams of FIG. 2F. This gap-repair cloning system can be taken advantage of to easily insert or clone full length variants or multiple regions with sufficient overlap, into a linearized vector. FIG. 2E depicts such a full length encoding nucleic acid 221 incorporated within the yeast genome 223. In certain embodiments, a plasmid is taken up by yeast, and the gene is not incorporated into the genome as such—the plasmid replicates as the yeast cell grows and the protein is expressed via an ectopic process. FIG. 2E shows the intact plasmid after yeast puts the full length gene together and also clones the gene into the plasmid using its inherent homologous recombination capabilities. In an alternative technique, recombination is accomplished by a form of overlap extension PCR. In either approach, some overlap (e.g., at least 10, at least 20 or at least 30 nucleotide bases) should be provided between the region-specific nucleic acid sequences employed in the recombination process. No primers need be employed. In order for either technique to work, the individual region fragments employed in the recombination process must share some overlapping sequence at the edges of their respective regions. This is shown in FIG. 2D by overlap sequence 231 between the first and second regions and overlap sequence 233 between the second and third regions.

IV. Implementation Options

Reference and Parent Sequences—

The methods described herein may make use of a "reference sequence" having multiple regions. Further, multiple mutations are provided over the regions of the reference sequence. The mutant proteins (variants) harboring these mutations may be derived directly or indirectly from the reference sequence. Further, the mutations may be introduced at any of multiple points in the overall peptide discovery process. For example, they may be identified as part of a primary screen of protein variants produced from saturation mutagenesis. At some point, the mutations are incorporated into downstream variants by region shuffling.

In some embodiments, each such variant is derived from the same ancestor or parent protein and contains at least one mutation as compared to the parent protein.

The parent protein need not have an amino acid sequence identical to the amino acid sequence of the wild type protein. However, in some embodiments, the parent protein is the wild type protein. In some embodiments, the parent protein has been mutated as compared to the wild type protein. The reference protein sequence itself may be that of the parent or ancestral protein or it may be consensus sequence derived from a group of proteins have a common property, e.g., a family of proteins. In some cases, other reference sequences may be defined. A non-limiting representative list of families or classes of enzymes which may be mutagenized in accordance with aspects of the present disclosure includes the following oxidoreducatses (E.C.1); transferases (E.C.2); hydrolyases (E.C.3); lyases (E.C.4); isomerases (E.C.5) and ligases (E.C.6). More specific but non-limiting subgroups of oxidoreducatses include dehydrogenases (e.g., alcohol dehydrogenases (carbonyl reductases), xylulose reductases, aldehyde reductases, farnesol dehydrogenase, lactate dehydrogenases, arabinose dehydrogenases, glucose dehyrodgenase, fructose dehydrogenases, xylose reductases and succinate dehyrogenases), oxidases (e.g., glucose oxidases, hexose oxidases, galactose oxidases and laccases), monoamine oxidases, lipoxygenases, peroxidases, aldehyde dehydrogenases, reductases, long-chain acyl-[acyl-carrier-protein] reductases, acyl-CoA dehydrogenases, ene-reductases, synthases (e.g., glutamate synthases), nitrate reductases, mono and di-oxygenases, and catalases. More specific but non-limiting subgroups of transferases include methyl, amidino, and carboxyl transferases, transketolases, transaldolases, acyltransferases, glycosyltransferases, transaminases, transglutaminases and polymerases. More specific but non-limiting subgroups of hydrolases include ester hydrolases, peptidases, glycosylases, amylases, cellulases, hemicellulases, xylanases, chitinases, glucosidases, glucanases, glucoamylases, acylases, galactosidases, pullulanases, phytases, lactases, arabinosidases, nucleosidases, nitrilases, phosphatases, lipases, phospholipases, proteases, ATPases, and dehalogenases. More specific but non-limiting subgroups of lyases include decarboxylases, aldolases, hydratases, dehydratases (e.g., carbonic anhydrases), synthases (e.g., isoprene, pinene and farnesene synthases), pectinases (e.g., pectin lyases) and halohydrin dehydrogenases. More specific, but non-limiting subgroups of isomerases include racemases, epimerases, isomerases (e.g., xylose, arabinose, ribose, glucose, galactose and mannose isomerases), tautomerases, and mutases (e.g. acyl transferring mutases, phosphomutases, and aminomutases. More specific but non-limiting subgroups of ligases include ester synthases. This list, while illustrating certain specific aspects of the possible enzymes of the disclosure, is not considered exhaustive and does not portray the limitations or circumscribe the scope of the disclosure.

In some cases, the candidate enzymes useful in the methods described herein may be capable of catalyzing an enantioselective reaction such as an enantioselective reduction reaction, for example. Such enzymes can be used to make intermediates useful in the synthesis of pharmaceutical compounds for example.

Production of Mutants—

The mutants are associated with particular regions where their mutations reside in the reference or parent polypeptide. In certain embodiments, the process used to introduce the mutations is controllable in a way that allows the resulting mutants (or sequences harboring those mutants) to be addressed or otherwise associated with the region of the reference sequence where the mutation occurs. Site directed mutagenesis is thus one example of a useful technique for introducing mutations for the methods described herein. Alternatively or in addition, the mutants may be provided by gene synthesis, saturating random mutagenesis, semi-synthetic combinatorial libraries of residues, directed evolution, recursive sequence recombination (RSR) (see, e.g., US Patent Application No. 2006/0223143, incorporated by reference herein in its entirety), gene shuffling, error-prone PCR, and the like. One example of a suitable saturation mutagenesis procedure is described in U.S. patent application Ser. No. 12/562,988 filed Sep. 18, 2009 by Colbeck et al. (US Published Patent Application No. 20100093560), which is incorporated herein by reference in its entirety.

In some embodiments, the mutations introduced into the parent or reference polypeptide have been (a) previously identified in the literature as affecting substrate specificity, selectivity, stability, or other beneficial property and/or (b) computationally predicted to improve protein folding patterns (e.g., packing the interior residues of a protein), ligand binding, subunit interactions, family shuffling between multiple diverse homologs, etc.

In some examples, the various mutants are grouped into sub-libraries as they are produced, such that the mutants having mutations in a first region are grouped in a first sub-library, the mutants having mutations in a second region are grouped in a second sub-library, and so on. In some cases, host cells produce the mutants generated in the initial stages of the methods described herein. In some aspects, the mutants are recombinantly expressed by such cells. In some aspects, the present disclosure provides a plurality of host cell colonies or cultures, where each colony or culture expresses one variant and the variants produced by the plurality all belong to the same sub-library.

Beneficial Properties—

After the genes for the polypeptide variants have been introduced into one or more host cells, the expressed mutant proteins having properties of interest are selected. The properties of interest can be any phenotypic or identifiable feature.

In some embodiments, a beneficial property or desired activity is an increase or decrease in one or more of the following: substrate specificity, chemoselectivity, regioselectivity, stereoselectivity, stereospecificity, ligand specificity, receptor agonism, receptor antagonism, conversion of a cofactor, oxygen stability, protein expression level, thermoactivity, thermostability, pH activity, pH stability (e.g., at alkaline or acidic pH), inhibition to glucose, and resistance to inhibitors (e.g., acetic acid, lectins, tannic acids and phenolic compounds). Other beneficial properties may include an altered profile in response to a particular stimulus; e.g., altered temperature and pH profiles. In some embodiments, the members of the plurality that act on the same substrate differ with respect to one or more of the following properties: rate of product formation, percent conversion of a substrate to a product, or percent conversion of a cofactor.

In some embodiments, the selected mutants are operable over a broad pH range, such as for example, from pH about 2 to pH about 14, from pH about 2 to pH about 12, from pH about 3 to pH about 10, from about pH 5 to about pH 10, pH about 3 to 8, pH about 4 to 7, or pH about 4 to 6.5. In some embodiments, the selected mutants are operable over a broad range of temperatures, such as for example, a range of from about 4° C. to 100° C., from about 4° C. to about 80° C., from about 4° C. to about 70° C., from about 4° C. to about 60° C., from about 4° C. to about 50° C., from about 25° C. to 90° C., from about 30° C. to 80° C., from about 35° C. to 75° C., or from about 40° C. to 70° C. In some embodiments, the selected mutants are operable in a solution containing from about 10 to about 50% or more percent organic solvent. Any of the above ranges of operability may be screened as a beneficial property or desired activity.

Screening—

Mutants may be screened for desired activity using any of a number of suitable techniques. For example, enzyme activity may be detected in the course of detecting, screening for, or characterizing candidate or unknown ligands, as well as inhibitors, activators, and modulators of enzyme activity. Fluorescence, luminescence, mass spectroscopy, radioactivity, and the like may be employed to screen for beneficial properties. Screening may be performed under a range of temperature, pH, and or solvent conditions.

Various detectable labels may be used in screening. Such labels are moieties that, when attached to, e.g., a polypeptide, renders such a moiety detectable using known detection methods, e.g., spectroscopic, photochemical, electrochemiluminescent, and electrophoretic methods. For such embodiments, the label may be a direct label, e.g., a label that is itself detectable or produces a detectable signal, or it may be an indirect label, e.g., a label that is detectable or produces a detectable signal in the presence of another compound. The method of detection will depend upon the label used, and will be apparent to those of skill in the art. Examples of suitable labels include radiolabels, fluorophores, chromophores, chelating agents, particles, chemiluminescent agents and the like. Such labels allow detection of labeled compounds by a suitable detector, e.g., a fluorometer. Suitable radiolabels include, by way of example and not limitation, $^3$H, $^{14}$C, $^{32}$P, $^{35}$S, $^{36}$Cl, $^{57}$Co, $^{131}$I and $^{186}$Re.

Fluorescent dyes when conjugated to other molecules or substances generate fluorescence signals that are detectable using standard photodetection systems such as photodetectors employing, e.g., a series of band pass filters and photomultiplier tubes, charged-coupled devices (CCD), spectrographs, etc., as exemplified by the systems described in U.S. Pat. Nos. 4,230,558 and 4,811,218 or in Wheeless et al., 1985, Flow Cytometry: Instrumentation and Data Analysis, pp. 21-76, Academic Press, New York, each incorporated herein by reference in its entirety.

Mass spectrometry encompasses any suitable mass spectrometric format known to those of skill in the art. Such formats include, but are not limited to, Matrix-Assisted Laser Desorption/Ionization, Time-of-Flight (MALDI-TOF), Electrospray (ES), IR-MALDI (see, e.g., PCT Application No. WO 99/57318 and U.S. Pat. No. 5,118,937, incorporated herein by reference in its entirety) Ion Cyclotron Resonance (ICR), Fourier Transform and combinations thereof.

"Chromophore" refers to a moiety with absorption characteristics, i.e., are capable of excitation upon irradiation by any of a variety of photonic sources. Chromophores can be fluorescing or nonfluorescing, and includes, among others, dyes, fluorophores, luminescent, chemiluminescent, and electrochemiluminescent molecules.

Examples of suitable indirect labels include enzymes capable of reacting with or interacting with a substrate to produce a detectable signal (such as those used in ELISA and EMIT immunoassays), ligands capable of binding a labeled moiety, and the like. Suitable enzymes useful as indirect labels include, by way of example and not limitation, alkaline phosphatase, horseradish peroxidase, lysozyme, glucose-6-phosphate dehydrogenase, lactate dehydrogenase and urease. The use of these enzymes in ELISA and EMITimmunoassays is described in detail in Engvall, 1980, Methods Enzym. 70: 419-439 and U.S. Pat. No. 4,857,453, each incorporated herein by reference in its entirety.

Screening generally selects only those mutants having a desired phenotype or combination of phenotypes. In many embodiments, mutants are selected only if they meet or exceed a prespecified threshold, which typically exceeds the level of the parent polypeptide. In some embodiments, however, variants may be selected for inclusion if they have only the same level of activity as the parent. This approach can be useful for generating neutral diversity which could later be useful in combination with other mutations.

Pooling DNA—

The mutants selected from each sub-library are pooled such that each sub-library contains mutants having mutations in the same region of the reference sequence. Thus, each pool is associated with a particular region of the reference sequence. Typically, a given pool contains only members (nucleotides/peptides) that have a mutation in the associated region. Usually, the members do not contain mutations outside the associated region.

The members may be provided as host cell colonies identified as expressing beneficial mutations in the region. However, the grouping may be accomplished using alternatives to cell colonies such as liquid cultures or supernatants. Often the associated pellets are pooled rather than the colonies themselves.

The nucleic acids encoding the full length mutant proteins may be extracted from host cells (or colonies thereof) by various techniques known to those skilled in the art. Such techniques include PCR, restriction enzyme digestions and the like. The resulting DNA encoding the mutants of a particular sub-library is pooled.

Isolating Region Sequences—

The nucleic acid sequences encoding the region associated with their particular pool are isolated. It should be understood that isolation does not necessarily involve amplification, although selective amplification is a particularly useful isolation technique. Other isolation techniques selectively cut the full length sequences near the boundaries of the regions, and then separate the resulting fragments. Such other techniques include restriction enzyme digestions. In an alternative approach, the mutations are defined ahead of time and the region DNA harboring these mutations is synthesized for some or all variants.

With any isolation technique, it is typically sufficient to remove the portions of the sequences that lie outside the region of interest. Ultimately a goal of isolation is to produce mutation rich pools of nucleic acids that align with specific regions of the reference sequence.

In one non-limiting example provided for the purpose of illustration only, assume that 75 individual colonies harboring 75 high-performing mutants are identified. Assume further that 15 of these mutants have mutations in a first region of the reference sequence. Possibly, the 60 remaining mutants are distributed over 4 other regions of the reference sequence. The 15 colonies and their associated mutants in the first region are then grouped into a first sub-library corresponding to the first region of the reference sequence. The 60 remaining mutants are grouped into 4 other sub-libraries.

In certain embodiments, DNA for the identified mutants is contained in plasmids which are extracted from the identified colonies. In the specific example described here, the plasmids containing the nucleic acid sequences encoding the 15 mutations in the first region are extracted from the 15 identified colonies and are pooled for simultaneous isolation of the first region subsequence. The pooling and isolation operations are typically performed without identifying the specific beneficial mutations giving rise to the high-performing mutants, which mutants are identified based on the selective pressure in the screen. Thus, the pooling and isolation operations may be performed expeditiously without the need to sequence the encoding DNA or the expressed protein for the selected mutants.

Returning again to the specific non-limiting example of 15 high-performing mutants harboring mutations within the first region, the plasmid DNA for the mutants of the first region may be isolated by various techniques as mentioned. In a specific embodiment, plasmid DNA is isolated using an available kit, such as one supplied by Qiagen N.V. (Germantown, Md.) or Macherey Nagel, Inc. (Bethlehem, Pa.). Taking the isolated plasmid DNA, a set of primers chosen to bracket the nucleic acid in the first region is then used to amplify the nucleic acid in this region. In designing such primers and then conducting PCR, only the nucleic acid in the first region of the plasmids is amplified, thereby isolating the nucleic acid sequence of the first region from the nucleic acid sequences of the other regions of the full-length gene encoding the mutants. Collectively, the amplified pooled nucleic acid from the first region contains 15 distinct sequences encoding the first region in this particular example.

The isolation (which is effected via amplification in this example) may be simultaneously performed on all members (fragments) of the pooled plasmid-based nucleic acid from the first region. This need not be the case, however. In alternative embodiments, the first region DNA from one or more of the high-performing mutants may be separately isolated and/or amplified. Thus, for example, seven of the 15 high-performing mutants may have their first region DNA pooled and amplified together, while the remaining eight high-performing mutants have their DNA separately pooled and amplified.

Figure 4:
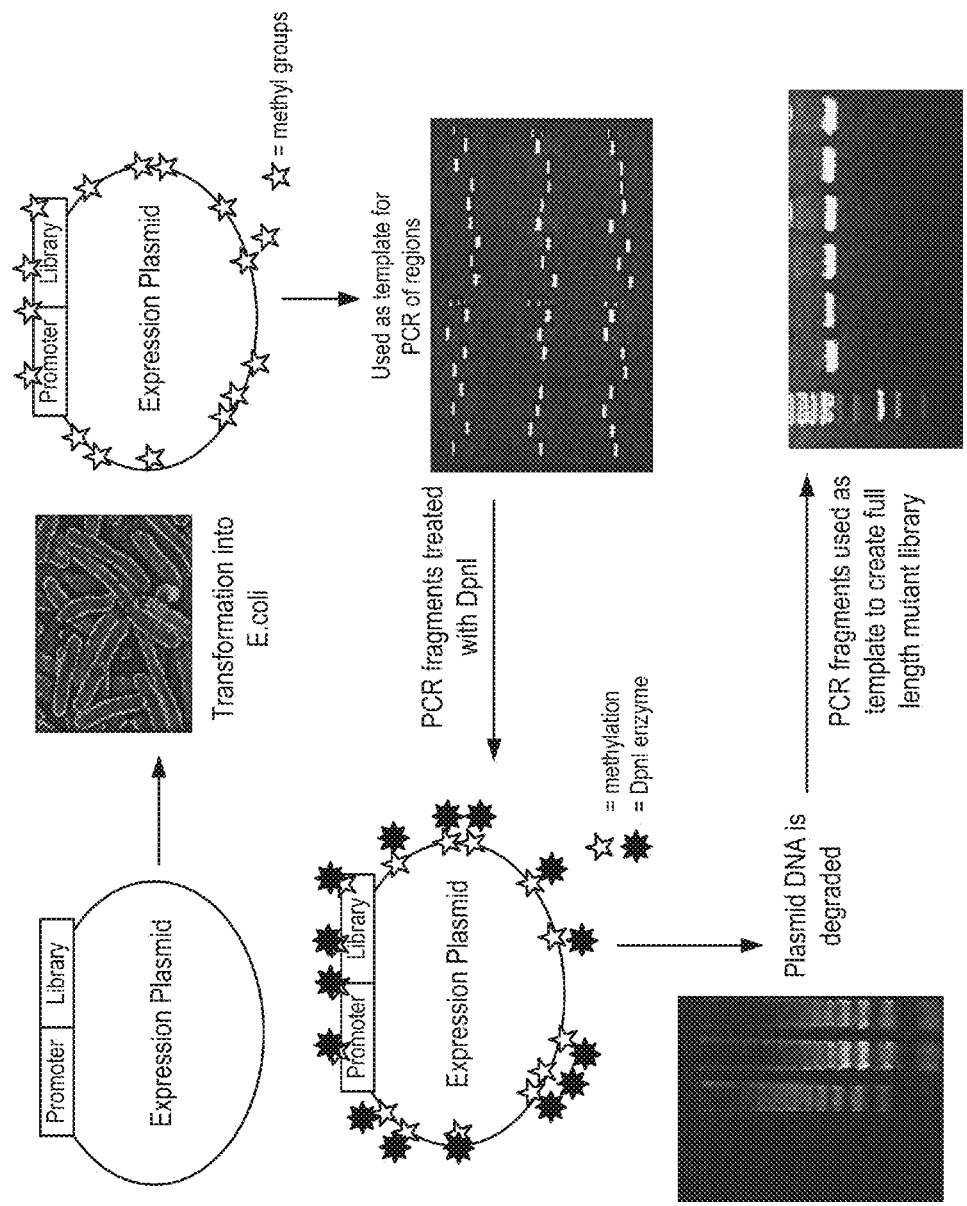
FIG. 4 depicts a plasmid template degradation process employing DpnI enzyme.

Once the regions are amplified/isolated to enrich for mutations, the individual region fragments may be enzymatically treated with the DpnI enzyme in order to remove the plasmids used as template. In many bacteria such as some of those that may be used to produce colonies expressing variants of the sub-libraries, DNA sequences are methylated throughout the genome as part of the cells' restriction modification system. The methylase enzyme recognizes a specific sequence and methylates one of the bases in that sequence. DNA which is amplified using PCR is not methylated, therefore, this inherent methylation system may be employed as the basis for the removal of plasmid DNA from the region PCR amplifications prior to combining the regions to reconstruct full length mutant variants. See for example FIG. 4 which depicts a plasmid template degradation process employing DpnI enzyme to remove the unamplified plasmid template.

Weighting the Contributions of the Mutations in a Region—

The pooled DNA isolated from a given region of the reference sequence may have each of the underlying beneficial mutations equally represented or, in other embodiments, one or more of the mutations may be over-represented. Thus, the individual sequences may be present in non-equimolar concentrations within the pool. In a specific embodiment, this unequal representation may be accomplished by biasing the pool of mutant DNA for a given region toward selected mutants prior to conducting amplification of the region under consideration. As a specific example, consider the case in which 15 mutants are identified that have mutations in the first region, and of those 15 mutations one performs 6 times better than the reference and the other 14 perform only 3 to 4 times better than the reference. The amount of starting material (or extracted DNA) from the 6 times better performing mutant that is added to the pool prior to amplification may significantly exceed the amount of material from the other less impressive mutants. The amplification product of this pool will over-represent the sequence (and associated mutation) for the mutant providing the 6 times better performance and hence the mutation will have a higher representation in the final variants in the resulting combinatorial library.

Multi-Section Regions—

Figure 3:
FIG. 3 is a schematic depiction of nucleic acid sequences for two different sub-regions of a region during an isolation process in accordance with certain embodiments.
Figure 3:
Figure 3:
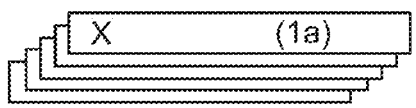
Figure 3:
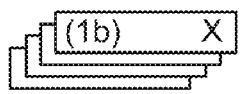
Figure 3:
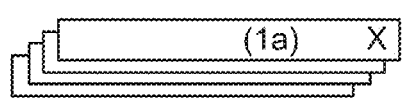
Figure 3:
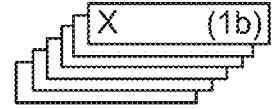

During isolation of regions having a single block of contiguous nucleotides, one pair of primers is all that is required for the amplification. For regions containing two or more contiguous blocks of nucleotides, typically two or more pairs of primers will be required. For such regions, all primer pairs may be used together in a single amplification reaction in a multiplex PCR format where each nucleotide block forms a separate amplicon in the reaction mixture. Alternatively, the primer pairs may be used in separate amplification reactions, where each contiguous block of nucleotides (amplicons) in a region is separately amplified. FIG. 3 illustrates isolation of a region having two separated blocks of contiguous nucleotides. A region may include three or more (e.g., four, five, six, seven, eight, or ten or more) such separated blocks.

Intra-Region Shuffling—

While the embodiments of region shuffling described above have focused on diversity generation through inter-region recombination, further embodiments of region shuffling include intra-region recombination or shuffling. For this intra-region shuffling embodiment diversity is introduced by shuffling mutations in a given region of the reference sequence. This embodiment of region shuffling can be conducted together with the region-to-region recombination or it can be conducted separately from such recombination.

The intra-region shuffling generally involves fragmenting the isolated nucleic acid sequences in a pool of such sequences. A pool typically contains only sequences of the region associated with the pool. Fragmenting the isolated nucleic acid sequences may be accomplished by various enzymatic techniques such as DNAse based techniques and related techniques (see e.g., Stemmer W. P. (1994) Rapid evolution of a protein in vitro by DNA shuffling; Nature, 370, 389-391; U.S. Pat. No. 5,605,793; U.S. Pat. No. 5,830,721; and U.S. Pat. No. 5,811,238, each incorporated herein by reference in its entirety) and uracil-based fragmentation (see e.g., U.S. Pat. No. 6,436,675 and Miyazaki (2002); Random DNA fragmentation with endonuclease V: application to DNA shuffling, Nucleic Acids Res. 2002 Dec. 15; 30(24): e139, both incorporated herein by reference).

In certain embodiments, fragments are produced by introducing uracil in an amplified DNA sequence and then cleaving the amplified sequences at the uracil positions. In one example, the wild type gene is PCR amplified while randomly incorporating dUTP (deoxyuracil triphosphate) in place of where dTTP (deoxythymidinetriphosphate) would normally occur. Some or all of the dTTP may be replaced. Uracil N-glycosylase and Endonuclease IV are used to fragment this PCR product by excision of uracil bases and phosphodiester bond cleavage at these sites, respectively. Some or all of the dTTP may be replaced. The amount of dTTP replaced depends on the degree of fragmentation to be achieved. The amplified region sequences, which incorporate uracil, are fragmented by digestion with, e.g., HK-Ung Thermolabile Uracil N-glycosylase and Endonuclease IV.

Various dTTP and dUTP ratios can be used to determine the degree of fragmentation which is desired. In various implementations, one may employ between about 1 through 6 mM dUTP concentrations. Example mixtures include the following:

| Volume for: | 1 mM dUTP | 3 mM dUTP | 5 mM dUTP |
| --- | --- | --- | --- |
| Sterile water | 60 | 60 | 60 |
| 100 mM dGTP | 10 | 10 | 10 |
| 100 mM dCTP | 10 | 10 | 10 |
| 100 mM dATP | 10 | 10 | 10 |
| 100 mM dTTP | 9 | 7 | 5 |
| 100 mM dUTP | 1 | 3 | 5 |

The uracil N-glycosylase excises uracil and leaves a nick, and Endonuclease IV completes the phosphodiester bond cleavage where nicks reside. The resulting fragmented regions are assembled using, e.g., PCR. In some cases, the assembly is performed using the fragments as produced in the uracil N-glycosylase-Endonuclease IV mixture. Assembly conditions are chosen to allow for base-pairing and extension of complementary fragments. Often, no primers are necessary. Each cycle of assembly PCR increases the average fragment length in the pool. The resulting nucleic acid sequences encoding the region in the pool contain a random assemblage of mutations contained in the original sequences making up a region pool (e.g., the mutations in sequences 215a-c in Pool A of FIG. 2B). In some embodiments, the assembly procedure is performed using only the fragments produced from a pool limited to sequences for a particular region of the reference sequence. The resulting reassembled nucleic acids with intra-region diversity is then combined with pools of nucleic acids from other regions to "rescue" or re-assemble full-length products which can be described as a library of variants containing random combinations of mutations from multiple regions and also including intra-region recombinations. In some embodiments, one or more of the nucleic acid pools from other regions is also subjected to intra-region shuffling prior to the inter-region recombination.

In some embodiments of region shuffling, the intra-region shuffling and the inter-region re-assembly operations are performed together in a single recombination process that spans some or all regions. These operations may involve, e.g., overlap extension PCR or homologous recombination in yeast. Regardless of the recombination technique employed, the nucleic acid fragments used in such intra- and inter-region recombination may be partially reassembled via an intra-region reassembly process prior to their use in the full length reassembly operation. For example, a few cycles of intra-region reassembly PCR may be performed on one or more pools of fragmented region-specific nucleic acid. Then in some embodiments prior to complete reassembly to produce the region length sequences, the partially assembled region fragments are combined with fragments from other regions to produce the full length nucleic acid sequences.

Figure 5A:
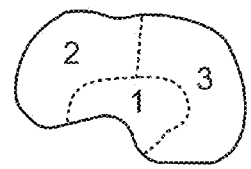
FIGS. 5A-C present a schematic depiction of recombination of nucleic acid sequences at various stages in an intra-region shuffling procedure.
Figure 5A:
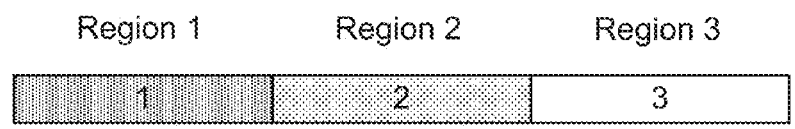
Figure 5A:
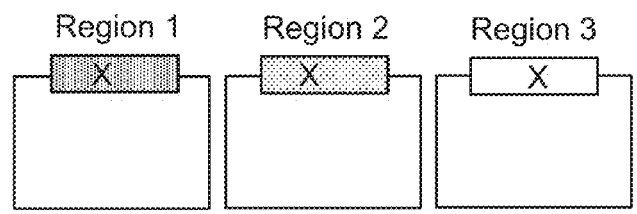
Figure 5B:
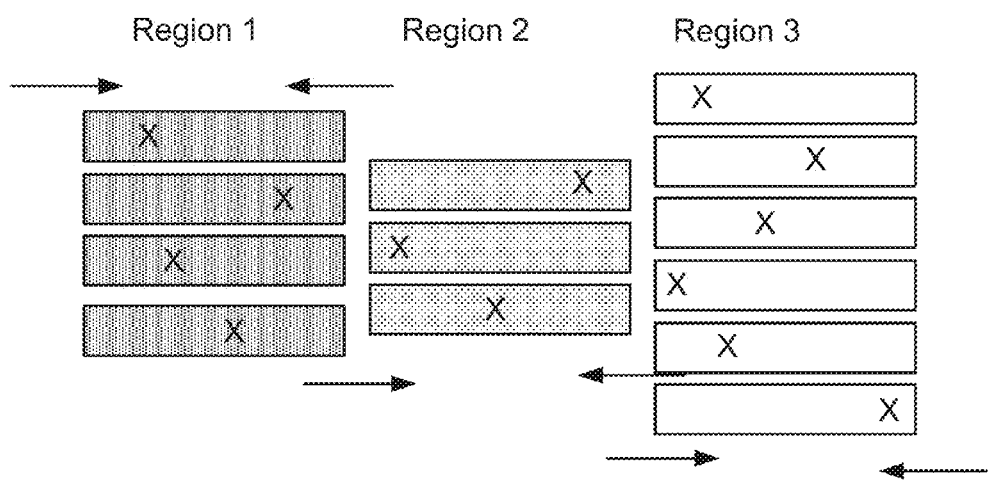
Figure 5C:
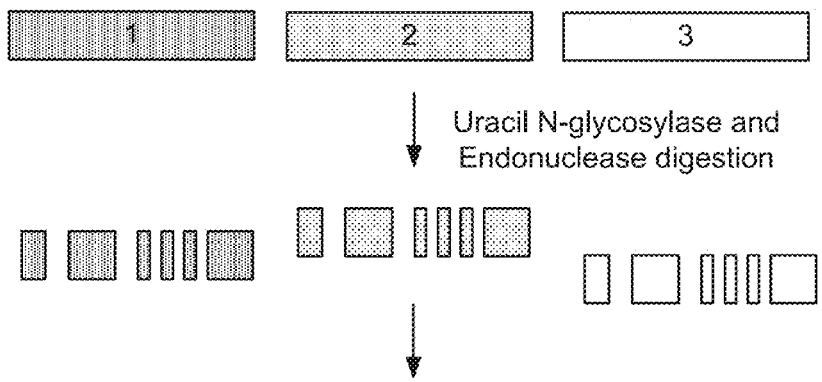
Figure 5C:

FIGS. 5A-4C depict one implementation of intra-region shuffling; specifically one in which full-length gene assembly is performed in one operation using intra-region fragments from multiple regions. As with inter-region shuffling procedures, the procedure begins by defining a parental gene into regions for pooling based on location of mutations. Mutations are introduced into the parental gene and then these mutations are grouped and screened based on the region in which they reside. Then the hits from each region are pooled for plasmid extraction. See FIG. 5A. Thereafter, as shown in FIG. 5B, this implementation of the intra-region shuffling process diverges from the inter-region shuffling procedure. Specifically, the isolation of each region's nucleic acid sequences is carried by PCR using dUTP in place of some of the dTTP that would normally be used in the PCR process. As mentioned this process randomly incorporates some uracil at in place of thymidine in the amplified nucleic acid of the region. Next in FIG. 5C, the amplified region fragments in each pool are subjected to fragmentation at the locations of the incorporated uracil by excision of uracil bases and cleavage of the nucleic acid backbone. As mentioned, Uracil N-glycosylase and Endonuclease IV may be used for this purpose. The resulting intra-region fragments are then used with SOE PCR (in this example) to create a full length recombinant library with mutations distributed through and across regions. The overlaps generated by the different sized fragments are typically sufficient to permit recombination.

Recombination—

The pools of isolated nucleic acid sequences are combined with each other to produce a collection of full length sequences. The process randomly or quasi-randomly combines the isolates of the individual regions with one another. The resulting recombinant polypeptides include a single isolate from each of the regions, stitched together in the order of the parent or reference sequence (e.g., region 1 is joined to region 2, region 2 is joined to region 3, etc.). Various techniques may be employed to ensure that this recombination occurs. Some of them employ introduction of overlap in isolates from adjacent regions.

Figure 6:
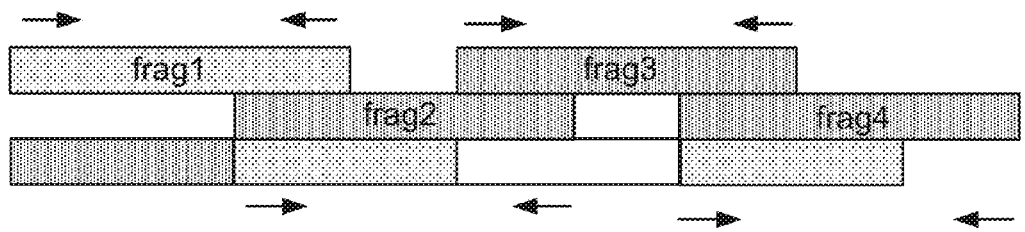
FIG. 6 is a schematic depiction of overlapping nucleic acid sequences isolated for contiguous regions in a full-length nucleic acid sequence.

If an amplification operation is employed to isolate the nucleic acid segments for the regions under consideration, the amplification reaction can be designed so that the amplicons produced for the various regions have overlapping sequences. For example, assuming that the first and second regions are adjacent, the amplification reaction can be designed so that the amplicon for the first region contains some terminal sequence that extends into second region's sequence. Similarly, the amplicon for the second region's amplification reaction may contain some terminal sequence that extends into the third region's sequence domain, and so on. This allows a recombination of the isolated fragments using overlap extension PCR or a related technique. The primers for the isolation methods may be designed so as to provide such overlap. See for example FIG. 6.

For homologous recombination in yeast, the overlap between fragments from adjacent regions may be about 35 nucleotides in length or longer (e.g., about 35-1000 bp). For example, about 35, 40, 45, 50, 60, 70, 80, 90, 100, 150, 200, 250, 300, 400, 500, 600, 700, 800, 900, or 1000 base pairs may be provided in the overlap. For overlap extension PCR, the overlap may be smaller, e.g., at least 25 bp nucleotides in length (e.g., about 25 to 35 bp). For example, about 25, 26, 27, 28, 29, 30, 31, 32, 33, 34, or 35 base pairs may be provided in the overlap.

Additional Iterations of Region Shuffling—

The combinatorial library (typically a DNA pool) that results from region shuffling can be used as the starting point for a standard combinatorial library in subsequent rounds. It may produce mutations that are themselves sufficiently beneficial to be used in commercial products.

In various embodiments, region shuffling is used in conjunction with a sequence-activity model or other quantitative relationship. In some cases, such relationships are used to identify mutations in one or more the nucleic acid segments for one or more regions. In certain embodiments, such relationships are derived from variant libraries produced by region shuffling. Sequence activity relationships so produced may be employed to facilitate further rounds directed evolution, including additional rounds of region shuffling. For example, a first set of mutants produced by region shuffling can be screened to identify at least one polypeptide having enhanced activity for a candidate substrate. The one or more polypeptides so identified from the first recombinant library can then be used as the basis for generating a fine-tuned, higher resolution second plurality for screening the candidate substrate. For example, particularly beneficial mutations appearing in the first library may be used to generate a sequence activity relationship that is then used identify additional mutations. Such mutations may be selected for a subsequent round of region shuffling. The operations of screening and using the results to generate still finer-tuned, still higher resolution pluralities of mutants can be reiterated. In this way, novel polypeptides with a desired activity can be identified. A first plurality can be screened with a novel, unknown or naive substrate or ligand and a second plurality populated with second generation variants is generated before testing with the novel, unknown or naive substrate or ligand.

In some embodiments, a sufficient number of variants of the library (e.g., greater than ten variants, greater than 12 variants, greater than 15 variants and also greater than 20 variants) exhibit activity on a candidate substrate so that protein sequence activity relationship (ProSAR)-type algorithms may be used to identify important beneficial and/or detrimental mutations among the active variants. The putative more beneficial mutations can then be selected for combination or high weighting in subsequent rounds of region shuffling. ProSAR-type algorithms are described in U.S. Pat. No. 7,783,428 (issued Aug. 24, 2010), U.S. Pat. No. 7,747,391 (issued Jun. 29, 2010), U.S. Pat. No. 7,747,393 (issued Jun. 29, 2010), and U.S. Pat. No. 7,751,986 (issued Jul. 6, 2010), each of which are incorporated herein by reference.

Expression—

Expression of recombinant polypeptides produced by region shuffling can be accomplished using well known techniques. Other mutants feeding into region shuffling may be similarly expressed. Typically, for recombinant production, a polynucleotide sequence encoding the peptide is inserted into an appropriate expression vehicle, e.g., a vector which contains the necessary elements for the transcription and translation of the inserted coding sequence, or in the case of an RNA viral vector, the necessary elements for replication and translation. The expression vehicle is then introduced (e.g., transformed) into a suitable target cell which will express the peptide. Depending on the expression system used, the expressed peptide is then isolated by procedures well-established in the art. Methods for recombinant protein and peptide production are well known in the art (see, e.g., Sambrook et al., 1989, Molecular Cloning A Laboratory Manual, Cold Spring Harbor Laboratory, N.Y.; and Ausubel et al., 1989, Current Protocols in Molecular Biology, Greene Publishing Associates and Wiley Interscience, N.Y. each of which is incorporated by reference herein in its entirety.)

A variety of host-expression vector systems may be utilized to express the polypeptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant plasmid or virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; animal cell systems. Cell-free in vitro polypeptide synthesis systems may also be utilized to express the polypeptides described herein.

The expression elements of the expression systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage lambda, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the $^{35}$S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of expression product, SV40-, BPV- and EBV-based vectors may be used with an appropriate selectable marker.

In cases where plant expression vectors are used, the expression of sequences encoding the polypeptides described herein may be driven by any of a number of promoters. For example, viral promoters such as the 35S RNA and 19S RNA promoters of CaMV (Brisson et al., 1984, Nature 310:511-514), or the coat protein promoter of TMV (Takamatsu et al., 1987, EMBO J. 6:307-311) may be used; alternatively, plant promoters such as the small subunit of RUBISCO (Coruzzi et al., 1984, EMBO J. 3:1671-1680; Broglie et al., 1984, Science 224:838-843) or heat shock promoters, e.g., soybean hsp17.5-E or hsp17.3-B (Gurley et al., 1986, Mol. Cell. Biol. 6:559-565) may be used (each incorporated by reference in its entirety). These constructs can be introduced into plant cells using Ti plasmids, Ri plasmids, plant virus vectors, direct DNA transformation, microinjection, electroporation, etc. For reviews of such techniques see, e.g., Weissbach & Weissbach, 1988, Methods for Plant Molecular Biology, Academic Press, N.Y., Section VIII, pp. 421-463; and Grierson & Corey, 1988, Plant Molecular Biology, 2d Ed., Blackie, London, Ch. 7-9 (each incorporated by reference in its entirety).

In one embodiment an insect expression system that may be used to produce the polypeptides described herein, *Autographa californica*, nuclear polyhedrosis virus (AcNPV) is used as a vector to express the foreign genes. The virus grows in *Spodoptera frugiperda* cells. A coding sequence may be cloned into non-essential regions (for example the polyhedron gene) of the virus and placed under control of an AcNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed (e.g., see Smith et al., 1983, J. Virol. 46:584; U.S. Pat. No. 4,215,051 (each incorporated by reference in its entirety)). Further examples of this expression system may be found in Current Protocols in Molecular Biology, Vol. 2, Ausubel et al., eds., Greene Publish. Assoc. & Wiley Interscience (incorporated by reference in its entirety).

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. (e.g., see Logan & Shenk, 1984, Proc. Natl. Acad. Sci. USA 81:3655-3659). Alternatively, the vaccinia 7.5 K promoter may be used, (see, e.g., Mackett et al., 1982, Proc. Natl. Acad. Sci. USA 79:7415-7419; Mackett et al., 1984, J. Virol. 49:857-864; Panicali et al., 1982, Proc. Natl. Acad. Sci. USA 79:4927-4931 (each incorporated by reference in its entirety)).

Non-limiting examples of fungal promoters include those derived from a cellulase gene isolated from a *Chrysosporium lucknowense* or a *Myceliophthora thermophilia* strain; or a promoter from a *T. reesei* cellobiohydrolase gene (reference is made to WO2010107303). Other examples of suitable promoters are promoters obtained from the genes of *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus* niger or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), promoters such as cbh1, cbh2, egl1, egl2, pepA, hfb1, hfb2, xyn1, amy, and glaA (Nunberg et al., 1984, *Mol. Cell Biol.*, 4:2306-2315, Boel et al., 1984, *EMBO J.* 3:1581-85 and EPA 137280) and mutant, truncated, and hybrid promoters thereof. In a yeast host, useful promoters can be from the genes for *Saccharomyces cerevisiae* enolase (eno-1), *Saccharomyces cerevisiae* galactokinase (gal1), *Saccharomyces cerevisiae* alcohol dehydrogenase/glyceraldehyde-3-phosphate dehydrogenase (ADH2/GAP), and *S. cerevisiae* 3-phosphoglycerate kinase. Other useful promoters for yeast host cells are described by Romanos et al., 1992, *Yeast* 8:423-488. Promoters associated with chitinase production in fungi may be used. See, e.g., Blaiseau and Lafay, 1992, *Gene* 120243-248 (filamentous fungus *Aphanocladium album*); Limon et al., 1995, *Curr. Genet*, 28:478-83 (*Trichoderma harzianum*).

In cell-free polypeptide production systems, components from cellular expression systems are obtained through lysis of cells (eukarya, eubacteria or archaea) and extraction of important transcription, translation and energy-generating components, and/or, addition of recombinant synthesized constituents (e.g., see Shimizu et al. Methods. 2005 July; 36(3):299-304; Swartz et al. 2004. Methods in Molecular Biology 267:169-182 (each incorporated by reference in its entirety)). Thus, cell-free systems can be composed of any combination of extracted or synthesized components to which polynucleotides can be added for transcription and/or translation into polypeptides.

Other expression systems for producing polypeptides described herein will be apparent to those having skill in the art. In some aspects, the present disclosure provides a plurality of host cell colonies or cultures, where each colony or culture expresses one variant and the variants produced by the plurality are all produced by the same region shuffling procedure.

The polypeptides described herein can be purified by art-known techniques such as reverse phase chromatography high performance liquid chromatography, ion exchange chromatography, gel electrophoresis, affinity chromatography and the like. The actual conditions used to purify a particular compound will depend, in part, on synthesis strategy and on factors such as net charge, hydrophobicity, hydrophilicity, etc., and will be apparent to those having skill in the art.

V. Parameter Ranges

The number of mutations that are incorporated in region shuffling (e.g., the number mutations in all the isolates of all region-based pools) will typically be at least about 10, at least about 20, at least about 50, at least about 70, at least about 100, at least about 200, at least about 500, at least about 700, at least about 1000, at least about 2000, at least about 5000, at least about 700, or at least about 10,000. In a specific embodiment, 200 sites in a reference sequence are used for mutations. Each of these sites may contain 20 different amino acids or some subset of the 20 naturally occurring amino acids.

Typically, the mutations in the reference protein span a significant fraction of the protein's length; in some cases its entire length. In various embodiments, the fraction of the reference protein spanned by the mutations is at least about 25%, or at least about 40%, or at least about 50%, or at least about 60%, or at least about 70%, or at least about 80%, or at least about 85%, or at least about 90%, or at least about 95%. The "fraction" spanned by the mutations is the portion of the reference protein's full length bounded by the edge mutations (e.g., the mutations closest to the N-terminus and closest to the C-terminus).

There will be at least two regions in the reference protein used for region shuffling. More typically there will be at least four such regions. In various embodiments, the number of regions in a sequence is at least about 3, or at least about 4 or at least about 10. For example, region shuffling may employ 2, 3, 4, 5, 6, 7, 8, 9, or 10 regions. Typically, the number of regions will be between about 3 and 10. It should be understood that the number of regions typically depends on the overall size of the protein, the bigger the protein the more regions one can create without encountering technical challenges when reassembling the fragments.

The size of a region is typically between about 100 and 1000 nucleotides (e.g., about 100, 150, 200, 250, 300, 350, 400, 450, 500, 550, 600, 650, 700, 750, 800, 850, 900, 950, or 1000 nucleotides). A region is typically, though not necessarily, a set of contiguous nucleotides. All regions may be roughly the same size, although this need not be the case. Frequently, they are of different sizes, varying by, e.g., as much as about 200%.

The pool for each region will contain at least one isolated sequence (e.g., at least one distinct sequence), although possibly numerous copies of it), and typically many more such sequences. In various embodiments, the number of distinct isolated sequences in the pool or sub-library associated with a region is at least about 5, or at least about 10, or at least about 25, or at least about 50, or at least about 75, or at least about 100.

Typically, the number of mutations within an isolated nucleic acid segment encoding a region is one. However, this need not be the case, particularly when intra-region shuffling is employed as discussed above. Thus, it will not be uncommon for pool members produced through intra-region shuffling to have two mutations or more. Of course, the actual number of mutations in any given sequence of the region (as well as the average number across all members in a given pool) depends on the size of the region and how the fragmentation reaction is set up. The number of mutations can be controlled to a degree if one varies the conditions to create, for example, fragments of about 20 bases in length for a given region of approximately 200 bases. In some embodiments, the average number of mutations in isolates in a given pool is about two or more, or about 3 or more.

In certain embodiments, the full-length sequences generated through recombination have at least one mutation per region. For example, the recombination reaction may employ only regions containing at least one mutation. Such embodiments do not employ wild-type sequences (or more generally reference sequences) for any regions used in the recombination reaction. When intra-region shuffling is applied to one or more of the pools, the full-length sequences may have significantly more than one mutation per region, on average.

The number of recombinant variants produced by region shuffling can be relatively large. Examples include at least about 20, 30, 40, 50, 60, 75, 100, 200, 300, 400, 500, 750 1000, 2500, 5000, 7500, 10,000 or more such recombinant variants. It should be understood that many implementations of region shuffling will not produce all combinations of mutations. Thus, not all combinations of mutations will be represented in the recombinant library produced through region shuffling. Rather the methods herein provide a way to focus on mutants having combinations of beneficial mutations without considering all possible combinations of mutations.

As an example, assume that there are 40 "hits" identified in the parental variants used for region shuffling. Assume that these hits contain mutations that are distributed over 4 regions, with 10 distinct mutations in each region. The number of theoretical derivative variants in the resulting library would be $10^4$ or 10,000, which might exceed an optimal number of variants to screen. In some embodiments, (at least 500 variants, at least 1,000 variants, at least 2,000 variants or at least 5,000 variants of all possible variants are produced and screened. In other embodiments, the number of variants that are produced and screened may be less than 500.

Frequently when exploring sequence space using conventional techniques, many resulting variants contain significant fractions of wild type sequence. As a consequence the impact of the one or few beneficial mutations may be "washed out." For example, if all of the variants that were selected as beneficial were combined using classical DNA shuffling, there would be an excess of wild type sequence to mutant sequence at any given position (e.g., no enrichment for the beneficial mutations at any given position or region). When the variants are recombined using classical DNA shuffling, the beneficial mutations are "hidden" amongst the wild type sequence and therefore classical DNA shuffling requires a much larger screening effort to identify the additive effects of combined mutations. By using region shuffling, one is able to "enrich" each region for beneficial mutations and therefore see a much higher rate of incorporation during recombination. Further, with region shuffling one is able to identify additive effects of beneficial mutations with significantly less screening effort. Because wash out is less of a concern in the techniques described herein, an exhaustive exploration of mutation combinations is typically not needed.

VI. Examples

Example 1

Region Shuffling to Identify Cellobiohydrolase Type 2b Variants

A region shuffling library was constructed from the full-protein saturation mutagenesis hits derived from a wild-type cellobiohydrolase (CBH2b) enzyme (SEQ ID NO:1). The term "cellobiohydrolase" ("CBH"), refers to a category of cellulases (EC 3.2.1.91) that hydrolyze glycosidic bonds in cellulose. CBH type 2 is a cellobiohydrolase belonging to the glycoside hydrolase family 6 (GH6) family of cellulases and which is also commonly called "the Cel6 family." Cellobiohydrolases of the GH6 family are described, for example, in the Carbohydrate Active Enzymes (CAZY) database, accessible on the world wide web at cazy.org/GH6.html. Other terms typically used to describe CBHs are exoglucanses and 1,4-beta-cellobiohyrolases.

The wild-type CBH2b protein (SEQ ID NO:1) was divided into 8 regions (Region 1 including amino acids 1-76, Region 2 including amino acids 77-135, Region 3 including amino acids 136-194, Region 4 including amino acids 195-253, Region 5 including amino acids 254-312, Region 6 including amino acids 313-371, Region 7 including amino acids 372-430, and Region 8 including amino acids 431-482). DNA corresponding to those regions plus about 30 bases of overlap on each side was PCR amplified (conditions in Table 1 below) from a pool of DNA known to contain favorable variants with mutations in those regions. Each region contained between 0 and 20 distinct mutations. The amount of template used for each variant was identical. After the PCR amplifications of the regions were performed, the resulting pools of DNA were reassembled using primerless PCR and then rescued using a second PCR operation using primers placed about 100 bp outside both ends of the gene. The second PCR operation filtered out non-full length fragments. Its conditions are presented in Table 2. The rescued DNA was ligated into an expression vector and transformed into *E. coli*. The resulting library was plated and colonies were picked for growth and an activity assay. The activity assay described in Example 3 was used.

TABLE 1 cbh Region Amplification Conditions

| PCR | µL |
| --- | --- |
| Water | 32.5 |
| 5X Phusion GC buffer (New England Biolabs, Inc., MA) | 10 |
| DMSO | 2 |
| 10 mM dNTPs | 2 |
| Backbone Plasmid (final 1 ng/uL) | 1 |
| Phusion Polymerase | 0.5 |
| Total volume | 48 |
| Oligo Pooladded separately | 2 |

| Operations | Temp ° C. | Time |
| --- | --- | --- |
| 1 | 95 | 2 min. |
| 2 | 95 | 30 sec. |
| 3 | 56 | 30 sec. |
| 4 | 72 | 30 sec. |
| 5 | 72 | 5 min. |
| 6 | 10 | Hold |

Operations 2-4 are repeated 25X

TABLE 2 cbh Assembly PCR Conditions

| Assembly of Fragments | µL |
| --- | --- |
| Water | 31.5 |
| 5X Phusion GC buffer | 10 |
| DMSO | 2 |
| 10 mM dNTPs | 1 |
| Phusion Polymerase | 0.5 |
| Total volume | 45 |
| Fragment Pool—add sep. | 5 |

| Operations | Temp. | Time |
| --- | --- | --- |
| 1 | 95° C. | 2 min. |
| 2 | 95° C. | 30 sec. |
| 3 | 46° C. | 30 sec. |
| 4 | 72° C. | 30 sec. |
| 5 | 72° C. | 3 min. |
| 6 | 10° C. | Hold |

Repeat operations 2-4: 20X

TABLE 3 cbh Rescue PCR Conditions

| Rescue PCR | 1rxn |
|---|---|
| Water | 27.5 |
| 5X Phusion GC buffer | 10 |
| DMSO | 2 |
| 10 mM dNTPs | 1 |
| F oligo (10 µM) | 2 |
| R oligo (10 µM) | 2 |
| Phusion Polymerase | 0.5 |
| Total volume | 45 |
| Assembly fragments—Added separately | 5 |

| Operations | Temp. ° C. | Time |
|---|---|---|
| 1 | 95 | 2 min. |
| 2 | 95 | 30 sec. |
| 3 | 56 | 30 sec. |
| 4 | 72 | 30 sec. |
| 5 | 72 | 5 min. |
| 6 | 10 | Hold |

Operations 2-4 are repeated 25X

TABLE 4

| Mutations with respect to wildtype | FIOP |
|---|---|
| S121D, S353N, E422P, W466R | +++ |
| V30G, H143R, S356Q, S454P | +++ |
| Y137H, Q186R, A270T | +++ |
| N37P, S353N, T476N | +++ |
| Q182P, I244M, S353N, S454G | ++ |
| T117G, E318K, S353N | ++ |
| S118R, P197Q, S353N | ++ |
| I244M, S353N | ++ |
| S84R, S353N, G401T, N479H | ++ |
| D136R, I244M, S353N, L373P, S376D | ++ |
| Q186R, I244H, W309A, S353N, P380D | ++ |
| S118R, S353N, P380H | ++ |
| T71A, Y137K, P380T, Q398L, T476R | ++ |
| V30G, I244M, S353N, P380D | ++ |
| I244M, S353T, S356W | ++ |
| G328Q, S353N, S443R | ++ |
| Q182P, S353N | ++ |
| N37P, K288R, S353N, Q398L, S440G | ++ |
| N37P, I244Q, V284L, S353K, S454P, P481Q | ++ |
| R24S, Q314R, A377T, T476R | + |
| Q182P, A377T | + |
| N37P, A156P, Q186R, I244Q, S350T, S454P | + |
| N37P, S350T, A377T, T476G | + |
| N37P, G328Q, S376K, G420T | + |
| I244Q, A377K, A445P | + |
| S118R, S356Q, P380H, Q398L | + |
| N37P, G420T | + |
| S350T, A377G | + |
| T117N | + |

Example 2

High Throughput Assays to Identify CBH2b Variants Made by the Region Shuffling Methods cDNA sequences made from the region shuffling method of Example 1 were used to make plasmid libraries containing the variant CBH genes and they were transformed into *S. cerevisiae*. Cells were grown on media and under conditions known in the art and then transferred into 96-well microtiter plates (deep well) containing 380 µL Defined Expression Medium with extra amino acids ("DEMA Extra") broth (20 g/L glucose, 6.7 g/L yeast nitrogen base without amino acids (SigmaY-0626), 5 g/L ammonium sulphate, 24 g/L amino acid mix minus uracil (United States Biological D9535); pH approximately 6.0) containing 1% galactose. The plates were further incubated and were centrifuged after 48 hours at 4000 rpm for 15 minutes.

The clear media supernatant containing secreted CBH2b was used for a high throughput (HTP) thermostability assay using Avicel. In the thermostability assay, the supernatant samples were pre-incubated at pH 4.5, temperature 67-75° C. for 1-18 hours. The residual enzyme activity with and without the thermal challenge was measured as glucose production using a GOPOD cellulose-based assay (substrate: 200 g/L Avicel (Sigma); pH 5.0; temperature 50° C.; time: 24 hrs). Table 4 summarizes the results of the thermostability screen, which identified CBH2b variants using the region shuffling methods described herein. The thermostability of the CBH2b variants was compared to the thermostability of the wild-type CBH2b of SEQ ID NO:1 and presented as fold improvement over the parent (FIOP), wherein "+" indicates a FIOP of 1.0 to less than 2.0, "++" indicates a FIOP of 2.0 to less than 3.0, and "+++" indicates a FIOP of 3 or greater. Thermostability was assessed by determining residual enzyme activity on microcrystalline cellulose (Avicel, Sigma) after incubation at pH 4.5 and 67° C. for 1 hour. Mutations are indicated with respect to the wild-type CBH2b sequence. Amino acid positions (e.g., "W309") and changes (e.g., "W309A") are relative to SEQ ID NO:1.

Example 3

Improved Fatty Acid Reductase (FAR) Variants Made by Region Shuffling

A region shuffle library was constructed from the full-protein saturation mutagenesis hits derived from a wild-type 512 amino acid enzyme (SEQ ID NO:2). The hits were selected using an assay measuring retention times of fatty alcohols as described in Example 4. The protein was divided into 4 overlapping regions (Region 1 including amino acids 1-170, Region 2 including amino acids 140-335, Region 3 including amino acids 315-465, and Region 4 including amino acids 435-513) to provide about 80 bases of overlap in sections of DNA with minimal mutations. There were about 20-60 distinct mutations per region. DNA corresponding to those regions was PCR separately amplified from weighted pools of DNA known to contain favorable variants with mutations in those regions. Individual mutants were weighted based upon their assay performance, with higher performing mutants being accorded greater weights. The culture volume of each variant was weighted between 10 ul and 60 ul, favoring the better variants disproportionately using data from the activity assay. It was assumed that the encoding DNA of each variant was present in roughly the same concentration in each culture.

PCR amplifications of the regions were conducted in the presence of uracil, with dUTP and dTTP being present in equal concentrations, e.g., 5 mM. The other three dNTPs were provided each at a concentration of 10 mM. Four separate pools were amplified, each with its own unique primer set. The PCR amplification was conducted on pools under the conditions described in Example 1, except that the 10 mM dTTP was replaced with dUTP and dTTP concentration just mentioned.

The resulting pools of PCR fragments corresponding to each region were pooled and digested with Uracil DNA Glycosylase (UNG) and Endonuclease IV to fragment them further. Thus, the pools for the distinct regions were themselves pooled into one reaction mixture for digestion. After digestion, reassembly was performed by PCR under conventional conditions. Subsequently, rescue PCR was performed using flanking primers. The primers hybridized outside of the full length fatty acid reductase encoding sequence about 100 bp upstream of the sequence and 30 bp downstream of the sequence.

The digest was performed in PCR buffer (buffer supplied with the Herculase polymerase). The enzymes were pre-mixed in a "Uracil Excision Mix" from Epicentre. DpnI was added to remove the plasmid template. The amounts, in microliters, of the components of the reaction mixture were as follows: PCR sample 45; 1× Herculase Buffer 10; 10 mM dNTPs 2; Uracil Excision Mix 2; DpnI 1 and $H_2O$ 40. The reaction cycle was conducted for 2 hours at 37° C. and 2 min at 95° C.

There was no purification operation between digestion and reassembly. The fragments were simply diluted in a PCR dilution mix (see Table 5 below) and Herculase polymerase was added. (If there were no dNTPs in the fragmentation mix the dNTPs' concentrations would change during the dilution operation).

TABLE 5

Assembly PCR components in μL (FAR)

| PCR dilution mix: | |
|---|---|
| 10 × Herculase Buffer | 40 |
| 10 mM dNTPs | 8 |
| H2O | 352 |
| Assembly operation: | |
| Add 0.5 μl Herculase and cycle: | |
| 95° C. | 2 min. |
| 95° C. | 30 sec. |
| 44° C. | 30 sec. ⎤ |
| 72° C. | 30 sec. ⎦ 25x |
| 72° C. | 2 min. |

TABLE 6

Rescue PCR components in μL (FAR)

| Template | 2 |
|---|---|
| 10 × Herculase Buffer | 5 |
| 10 mM dNTPs | 1 |
| DMSO | 2 |
| FOR Primer | 0.25 |
| REV Primer | 0.25 |
| Herculase | 0.5 |
| H2O | 39 |
| 95° C. | 2 min. |
| 95° C. | 15 sec. |
| 56° C. | 15 sec. ⎤ |
| 72° C. | 1 min. ⎦ 25x |
| 72° C. | 2 min. |

The DNA was ligated into a plasmid for expression of heterologous genes in E. coli, expression vector pCK11900. This expression vector is depicted in FIG. 3 of U.S. Patent Publication No. 2006/0195947, which is incorporated herein by reference in its entirety. The resulting library was plated and colonies were picked for growth and activity assay as described below.

Example 4

Evaluation of FAR Variants Made by Region Shuffling with Improved Fatty Alcohol Production FAR variants produced by the region shuffling methods descried herein were grown in 96-well plates and the FAR gene was expressed. Variants were analyzed by GC-FID and fatty alcohol production was measured. Table 7 provides the relative fatty alcohol production of the region shuffling variants for illustrative variants relative to a variant of wild-type M. algicola DG893 FAR (SEQ ID NO:2), which variant was identified in an earlier round.

TABLE 8

| Sequence changes (with respect to parent) | FIOP GC, 40C, 10% Glu, 24 hrs |
|---|---|
| S134R; S283F; K433S; | 1.5 |
| S283M; K433S; Y500R; | 1.4 |
| V104I; K433S; | 1.4 |
| M365N; K433S; | 1.3 |
| Q377K; K433S; | 1.3 |
| N177Q; Q377K; K433S; | 1.3 |
| N177Q; K433S; Y500R; | 1.2 |
| S134R; V399T; K433S; | 1.2 |
| D376P; K433S; S452G; | 1.2 |
| I186G; K433S; | 1.2 |
| S134R; K433S; | 1.1 |
| L364I; K433S; | 1.1 |
| K433S; S452N; | 1.1 |
| A12T; S134R; K433S; | 1.1 |
| K433S; S452N; | 1.1 |
| S244H; K433S; | 1.0 |
| S188I; K433S; | 1.0 |
| K433S; Q474R; | 1.0 |
| R403S; K433S; Y500R; | 1.0 |
| K433S; Y500R; | 1.0 |
| G410N; K433S; | 1.0 |
| G14V; A88V; K433S; | 0.9 |
| G410H; K433S; | 0.9 |
| K433S; Q474R; D508S; | 0.9 |
| S244A; M413R; K433S; | 0.9 |
| K433S; Q474R; D508S; | 0.9 |
| L69E; K433S; | 0.9 |
| G9D; K433S; F440V; G487T; Y500H; | 0.9 |
| S244A; M413R; K433S; | 0.8 |
| G410H; K433S; | 0.8 |
| K433S; S452A; | 0.8 |
| N177Q; G410C; K433S; | 0.8 |
| G9D; K433S; Q474R; D508S; | 0.8 |
| K433S; G487R; | 0.8 |
| K433S; T436Q; | 0.8 |
| S339G; K433S; | 0.8 |
| K224R; K433S; | 0.8 |
| T430R; K433S; | 0.7 |
| D212R; A366V; K433S; G487S; | 0.7 |
| N177Q; G410C; K433S; | 0.7 |
| K433S; T511K; | 0.7 |
| A12T; K433S; S452G; | 0.7 |
| A63R; K433S; | 0.7 |
| V405A; K433S; G487R; | 0.7 |
| K433S; T511K; | 0.6 |
| N427K; K433S; | 0.6 |
| K359T; K433S; | 0.5 |
| N58D; S283M; K433S; | 0.5 |
| I315V; K433S; | 0.4 |

Sequence information:
SEQ ID NO: 1

>cbh2b wildtype (with signal peptide)
MAKKLFITAALAAAVLAAPVIEERQNCGAVWTQCGGNGWQGPTCCASGSTC

VAQNEWYSQCLPNSQVTSSTTPSSTSTSQRSTSTSSSTTRSGSSSSSSTTPPPVSS

PVTSIPGGATSTASYSGNPFSGVRLFANDYYRSEVHNLAIPSMTGTLAAKASA

VAEVPSFQWLDRNVTIDTLMVQTLSQVRALNKAGANPPYAAQLVVYDLPDR

DCAAAASNGEFSIANGGAANYRSYIDAIRKHIIEYSDIRIILVIEPDSMANMVTN

MNVAKCSNAASTYHELTVYALKQLNLPNVAMYLDAGHAGWLGWPANIQPA

AELFAGIYNDAGKPAAVRGLATNVANYNAWSIASAPSYTSPNPNYDEKHYIE

AFSPLLNSAGFPARFIVDTGRNGKQPTGQQQWGDWCNVKGTGFGVRPTANT

GHELVDAFVWVKPGGESDGTSDTSAARYDYHCGLSDALQPAPEAGQWFQA

YFEQLLTNANPPF*

```
MAKKLFITAALAAAVLAAPVIEERQNCGAVWTQCGGNGWQGPTCCASGSTCVAQNEWYSQCLPNSQVTSST
1234567890123456789012345678901234567890123456789012345678901234567890 1
         1         2         3         4         5         6         7

TPSSTSTSQRSTSTSSSTTRSGSSSSSSTTPPPVSSPVTSIPGGATSTASYSGNPFSGVRLFANDYYRSEV
2345678901234567890123456789012345678901234567890123456789012345678 9012
         8         9        10        11        12        13        14

HNLAIPSMTGTLAAKASAVAEVPSFQWLDRNVTIDTLMVQTLSQVRALNKAGANPPYAAQLVVYDLPDRDC
3456789012345678901234567890123456789012345678901234567890123456789 0123
        15        16        17        18        19        20        21

AAAASNGEFSIANGGAANYRSYIDAIRKHIIEYSDIRIILVIEPDSMANMVTNMNVAKCSNAASTYHELTV
4567890123456789012345678901234567890123456789012345678901234567890 1234
        22        23        24        25        26        27        28

YALKQLNLPNVAMYLDAGHAGWLGWPANIQPAAELFAGIYNDAGKPAAVRGLATNVANYNAWSIASAPSYT
5678901234567890123456789012345678901234567890123456789012345678901 2345
        29        30        31        32        33        34        35

SPNPNYDEKHYIEAFSPLLNSAGFPARFIVDTGRNGKQPTGQQQWGDWCNVKGTGFGVRPTANTGHELVDA
6789012345678901234567890123456789012345678901234567890123456789012 3456
        36        37        38        39        40        41        42

FVWVKPGGESDGTSDTSAARYDYHCGLSDALQPAPEAGQWFQAYFEQLLTNANPPF*
7890123456789012345678901234567890123456789012345678901 23
        43        44        45        46        47        48
```

Without signal peptide:
APVIEERQNCGAVWTQCGGNGWQGPTCCASGSTCVAQNEWYSQCLPNSQV

TSSTTPSSTSTSQRSTSTSSSTTRSGSSSSSSTTPPPVSSPVTSIPGGATSTASYSG

NPFSGVRLFANDYYRSEVHNLAIPSMTGTLAAKASAVAEVPSFQWLDRNVTI

DTLMVQTLSQVRALNKAGANPPYAAQLVVYDLPDRDCAAAASNGEFSIANG

GAANYRSYIDAIRKHIIEYSDIRIILVIEPDSMANMVTNMNVAKCSNAASTYHE

LTVYALKQLNLPNVAMYLDAGHAGWLGWPANIQPAAELFAGIYNDAGKPA

AVRGLATNVANYNAWSIASAPSYTSPNPNYDEKHYIEAFSPLLNSAGFPARFI

VDTGRNGKQPTGQQQWGDWCNVKGTGFGVRPTANTGHELVDAFVWVKPG

GESDGTSDTSAARYDYHCGLSDALQPAPEAGQWFQAYFEQLLTNANPPF

Sequence Information:
SEQ ID NO: 2

MATQQQQNGASASGVLEQLRGKHVLITGTTGFLGKVVLEKLIRTVPDIGGIHL

LIRGNKRHPAARERFLNEIASSSVFERLRHDDNEAFETFLEERVHCITGEVTES

RFGLTPERFRALAGQVDAFINSAASVNFREELDKALKINTLCLENVAALAELN

SAMAVIQVSTCYVNGKNSGQITESVIKPAGESIPRSTDGYYEIEELVHLLQDKI

SDVKARYSGKVLEKKLVDLGIREANNYGWSDTYTFTKWLGEQLLMKALSGR

-continued

```
SLTIVRPSIIESALEEPSPGWIEGVKVADAIILAYAREKVSLFPGKRSGIIDVIPVD

LVANSIILSLAEALSGSGQRRIYQCCSGGSNPISLGKFIDYLMAEAKTNYAAYD

QLFYRRPTKPFVAVNRKLFDVVVGGMRVPLSIAGKAMRLAGQNRELKVLKN

LDTTRSLATIFGFYTAPDYIFRNDSLMALASRMGELDRVLFPVDARQIDWQLY

LCKIHLGGLNRYALKERKLYSLRAADTRKKAA

MATQQQQNGASASGVLEQLRGKHVLITGTTGFLGKVVLEKLIRTVPDIGGIHLLIRGNKRHPAARERFLNE
12345678901234567890123456789012345678901234567890123456789012345678901
         1         2         3         4         5         6         7

IASSSVFERLRHDDNEAFETFLEERVHCITGEVTESRFGLTPERFRALAGQVDAFINSAASVNFREELDKA
234567890123456789012345678901234567890123456789012345678901234567890123456789012
         8         9        10        11        12        13        14

LKINTLCLENVAALAELNSAMAVIQVSTCYVNGKNSGQITESVIKPAGESIPRSTDGYYEIEELVHLLQDK
3456789012345678901234567890123456789012345678901234567890123456789012 3
        15        16        17        18        19        20        21

ISDVKARYSGKVLEKKLVDLGIREANNYGWSDTYTFTKWLGEQLLMKALSGRSLTIVRPSIIESALEEPSP
4567890123456789012345678901234567890123456789012345678901234567890123 4
        22        23        24        25        26        27        28

GWIEGVKVADAIILAYAREKVSLFPGKRSGIIDVIPVDLVANSIILSLAEALSGSGQRRIYQCCSGGSNPI
567890123456789012345678901234567890123456789012345678901234567890123 45
        29        30        31        32        33        34        35

SLGKFIDYLMAEAKTNYAAYDQLFYRRPTKPFVAVNRKLFDVVVGGMRVPLSIAGKAMRLAGQNRELKVLK
678901234567890123456789012345678901234567890123456789012345678901234 56
        36        37        38        39        40        41        42

NLDTTRSLATIFGFYTAPDYIFRNDSLMALASRMGELDRVLFPVDARQIDWQLYLCKIHLGGLNRYALKER
7890123456789012345678901234567890123456789012345678901234567890123 4567
        43        44        45        46        47        48        49

KLYSLRAADTRKKAA
890123456789012
        50        51
```

VII. Other Embodiments

While various specific embodiments have been illustrated and described, it will be appreciated that various changes can be made without departing from the spirit and scope of the invention(s). For example, all the techniques described above may be used in various combinations.

---

What is claimed is:

1. A method of introducing diversity into a reference protein sequence, the method comprising:
   (a) providing a first plurality of mutant proteins derived from the reference protein sequence, wherein the first plurality of mutant proteins each have one or more established beneficial properties and mutations in a first region of the reference protein sequence but not in substantially any other region of the reference protein sequence;
   (b) providing a second plurality of mutant proteins derived from the reference protein sequence, wherein the second plurality of mutant proteins each have one or more established beneficial properties and mutations in a second region of the reference protein sequence but not in substantially any other region of the reference protein sequence;
   (c) isolating a first group of nucleic acid segments from nucleic acids encoding the first plurality of mutant proteins, each nucleic acid segment in the first group encoding the first region of the reference protein sequence but not encoding substantially any other region of the reference protein sequence, wherein isolating the first group of nucleic acid segments is performed without first sequencing the first group of nucleic acid segments to identify the mutations in the first region;
   (d) isolating a second group of nucleic acid segments from nucleic acids encoding the second plurality of mutant proteins, each nucleic acid segment in the second group encoding the second region of the reference protein sequence but not encoding substantially any of the first region of the reference protein sequence, wherein isolating the second group of nucleic acid segments is performed without first sequencing the second group of nucleic acid segments to identify the mutations in the second region; and
   (e) assembling at least the isolated nucleic acid segments from (c) and (d) into full length nucleic acid sequences encoding new mutant proteins.

2. The method of claim 1, wherein the reference protein sequence is a wild type protein sequence.

3. The method of claim 1 or 2, further comprising generating the first and second plurality pluralities of mutant proteins by a process comprising introducing point mutations into the reference protein sequence.

4. The method of claim 1 or 2, further comprising generating the first and second plurality pluralities of mutant proteins by a process comprising performing saturation mutagenesis on the reference protein sequence.

5. The method of claim 1, wherein the first and second pluralities of mutant proteins contains, collectively, at least about 100 mutations.

6. The method of claim 1, wherein the first and second pluralities of mutant proteins collectively comprise mutants having beneficial mutations spread across the protein sequence.

7. The method of claim 1, further comprising grouping individual mutant proteins from the first and second pluralities of mutant proteins based on regions of the reference protein or peptide sequence where mutations occur.

8. The method of claim 1, wherein the first group of nucleic acid segments comprises at least about 10 distinct nucleic acid segments, each having a distinct sequence.

9. The method of claim 1, wherein isolating the first group of nucleic acid segments comprises amplifying the nucleic acid segments in the first group in a single amplification reaction.

10. The method of claim 9, wherein the amplifying is performed under conditions that do not substantially amplify nucleic acid segments encoding any regions other than the first region.

11. The method of claim 9, wherein isolating the second group of nucleic acid segments comprises amplifying the nucleic acid segments in the second group in a single second amplification reaction.

12. The method of claim 1, wherein the first group of nucleic acid segments comprises at least about 5 distinct nucleic acid segment sequences.

13. The method of claim 1, wherein isolating the first group of nucleic acid segments is performed without first identifying any mutation contained in the first group of nucleic acid segments.

14. The method of claim 1, further comprising isolating a third group of nucleic acid segments from nucleic acids encoding a third plurality of mutant proteins derived from the reference protein sequence, wherein the third plurality of mutant proteins each have one or more established beneficial properties and mutations in a third region of the reference but not in substantially any other region of the reference protein sequence, and wherein each nucleic acid segment in the third group encoding the third region of the reference protein sequence but not encoding substantially any of the first or second regions of the reference protein sequence.

15. The method of claim 1, further comprising isolating at least three more groups of nucleic acid segments, each encoding a different region of the reference protein sequence.

16. The method of claim 1, further comprising isolating at least five more groups of nucleic acid segments, each encoding a different region of the reference protein sequence.

17. The method of claim 1, further comprising, prior to (e) isolating at least two additional groups of nucleic acid segments, each encoding a different region of the reference protein sequence but not encoding substantially any of the other region of the reference protein sequence,
wherein (e) comprises assembling the isolated nucleic acid segments from the at least two additional group in addition to the isolated nucleic acid segments from (c) and (d) into full length nucleic acid sequences encoding new mutant proteins.

18. The method of claim 1, wherein assembling at least the isolated nucleic acid segments from (c) and (d) is performed without using nucleic acid segments exactly encoding a region of the reference protein sequence.

19. The method of claim 1, wherein the assembling in (e) is performed using an overlap extension Polymerase Chain Reaction.

20. The method of claim 1, wherein the assembling in (e) is performed without using primers.

21. The method of claim 1, wherein the assembling in (e) is performed using homologous recombination in yeast.

22. The method of claim 1, further comprising (f) identifying one or more recombinant proteins encoded by one or more full length nucleic acid sequences from (e), wherein the one or more recombinant proteins have at least one beneficial property.

23. The method of claim 1, wherein (c) to (e) are performed without determining sequences of the mutant protein sequences.

24. The method of claim 1, wherein the nucleic acid segments from (c) used to assemble the full length nucleic acid sequences in (e) are present in non-equimolar amounts during the assembling.

25. The method of claim 24, wherein the non-equimolar amounts are chosen based on one or more properties of associated mutant proteins harboring mutations encoded by the nucleic acid segments present in non-equimolar amounts.

26. The method of claim 1, wherein the reference protein is an enzyme.

27. The method according to claim 26, wherein the enzyme is a cellulase, reductase, transferase, transaminase, or isomerase.

28. The method of claim 1, further comprising:
assaying and sequencing the new mutant proteins; and
developing a sequence activity model from assay and sequence information for the new mutant proteins.

29. A method of introducing diversity into a reference protein sequence, the method comprising:
(a) providing a first plurality of mutant proteins derived from the reference protein sequence, wherein the first plurality of mutant proteins each have one or more established beneficial properties and mutations in a first region of the reference protein sequence but not in substantially any other region of the reference protein sequence;
(b) providing a second plurality of mutant proteins derived from the reference protein sequence, wherein the second plurality of mutant proteins each have one or more established beneficial properties and mutations in a second region of the reference protein sequence but not in substantially any other region of the reference protein sequence;
(c) amplifying a first group of nucleic acid segments derived from nucleic acids encoding the first plurality of mutant proteins in a single amplification reaction, wherein each nucleic acid segment in the first group encodes the first region of the reference protein sequence, but does not encode substantially any other region of the reference protein sequence, and wherein amplifying the first group of nucleic acid segments is performed without first sequencing the first group of nucleic acid segments to identify the mutations in the first region;
(d) amplifying a second group of nucleic acid segments derived from nucleic acids encoding the second plurality of mutant proteins in a second amplification reaction, wherein each nucleic acid segment in the second group encodes the second region of the reference protein sequence, but does not encode substantially any of the first region of the reference protein sequence, and wherein amplifying the second group of nucleic acid segments is performed without first sequencing the second group of nucleic acid segments to identify the mutations in the second region; and
(e) assembling at least the isolated nucleic acid segments from (c) and (d) into full length nucleic acid sequences encoding new mutant proteins.

30. The method of claim 29, further comprising, prior to (c), pooling the nucleic acid segments in the first group.

31. The method of claim 30, wherein the pooling comprises mixing at least about 10 distinct nucleic acid segment sequences in the first group.

32. The method of claim 29, wherein amplifying the first group of nucleic acid segments is performed using a single set of primers.

33. The method of claim 29, further comprising repeating (d) for a third group of nucleic acid segments encoding a third region of the reference protein sequence.

34. The method of claim 29, wherein the nucleic acid segments from (c) used to assemble the full length nucleic acid sequences in (e) are present in non-equimolar amounts during the assembling.

35. The method of claim 34, wherein the non-equimolar amounts are chosen based on one or more properties of the mutant proteins encoded by the isolated nucleic acid segments in the first group.

36. The method according to of claim 29, wherein the reference protein is an enzyme.

37. The method according to claim 36, wherein the enzyme is a cellulase, reductase, transferase, transaminase, or isomerase.

38. A method of introducing diversity into a reference protein sequence, the method comprising:
(a) providing a first plurality of mutant proteins and a second plurality of mutant proteins derived from the reference protein sequence, wherein the first plurality of mutant proteins each have one or more established beneficial properties and mutations in a first region of the reference protein sequence but not in substantially any other region of the reference protein sequence, and wherein the second plurality of mutant proteins each have one or more established beneficial properties and mutations in a second region of the reference protein sequence but not in substantially any other region of the reference protein sequence;
(b) amplifying a first group of nucleic acid segments derived from nucleic acids encoding the first plurality of mutant proteins, wherein each nucleic acid segment in the first group encodes the first region of the reference protein sequence, but does not encode substantially any other region of the reference protein sequence, and each nucleic acid segment in the first group encodes its own distinct mutation, which mutation is found in a mutant protein selected in (a);
(c) fragmenting and optionally recombining the amplified nucleic acids produced in (b) to thereby produce a pool of nucleic acids encoding the first region and having increased diversity;
(d) amplifying a second group of nucleic acid segments derived from nucleic acids encoding the second plurality of mutant proteins, wherein each nucleic acid segment in the second group encodes the second region of the reference protein sequence, but does not encode substantially any of the first region of the reference protein sequence, and each nucleic acid segment in the second group encodes its own distinct mutation, which mutation is found in a mutant protein selected in (a); and
(e) assembling at least the isolated nucleic acid segments from (c) and (d) into full length nucleic acid sequences encoding new mutant proteins.

* * * * *

SEQUENCE LISTING

```
<160> NUMBER OF SEQ ID NOS: 3

<210> SEQ ID NO 1
<211> LENGTH: 482
<212> TYPE: PRT
<213> ORGANISM: Myceliophthora thermophilia

<400> SEQUENCE: 1

Met Ala Lys Lys Leu Phe Ile Thr Ala Ala Leu Ala Ala Ala Val Leu
1               5                   10                  15

Ala Ala Pro Val Ile Glu Glu Arg Gln Asn Cys Gly Ala Val Trp Thr
                20                  25                  30

Gln Cys Gly Gly Asn Gly Trp Gln Gly Pro Thr Cys Cys Ala Ser Gly
            35                  40                  45

Ser Thr Cys Val Ala Gln Asn Glu Trp Tyr Ser Gln Cys Leu Pro Asn
        50                  55                  60

Ser Gln Val Thr Ser Ser Thr Thr Pro Ser Ser Thr Ser Thr Ser Gln
65                  70                  75                  80

Arg Ser Thr Ser Thr Ser Ser Ser Thr Arg Ser Gly Ser Ser Ser
                85                  90                  95
```

Ser Ser Ser Thr Thr Pro Pro Val Ser Ser Pro Val Thr Ser Ile
            100                 105                 110

Pro Gly Gly Ala Thr Ser Thr Ala Ser Tyr Ser Gly Asn Pro Phe Ser
    115                 120                 125

Gly Val Arg Leu Phe Ala Asn Asp Tyr Tyr Arg Ser Glu Val His Asn
    130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175

Asp Thr Leu Met Val Gln Thr Leu Ser Gln Val Arg Ala Leu Asn Lys
                180                 185                 190

Ala Gly Ala Asn Pro Pro Tyr Ala Ala Gln Leu Val Val Tyr Asp Leu
    195                 200                 205

Pro Asp Arg Asp Cys Ala Ala Ala Ser Asn Gly Glu Phe Ser Ile
210                 215                 220

Ala Asn Gly Gly Ala Ala Asn Tyr Arg Ser Tyr Ile Asp Ala Ile Arg
225                 230                 235                 240

Lys His Ile Ile Glu Tyr Ser Asp Ile Arg Ile Ile Leu Val Ile Glu
                245                 250                 255

Pro Asp Ser Met Ala Asn Met Val Thr Asn Met Asn Val Ala Lys Cys
                260                 265                 270

Ser Asn Ala Ala Ser Thr Tyr His Glu Leu Thr Val Tyr Ala Leu Lys
            275                 280                 285

Gln Leu Asn Leu Pro Asn Val Ala Met Tyr Leu Asp Ala Gly His Ala
290                 295                 300

Gly Trp Leu Gly Trp Pro Ala Asn Ile Gln Pro Ala Ala Glu Leu Phe
305                 310                 315                 320

Ala Gly Ile Tyr Asn Asp Ala Gly Lys Pro Ala Ala Val Arg Gly Leu
                325                 330                 335

Ala Thr Asn Val Ala Asn Tyr Asn Ala Trp Ser Ile Ala Ser Ala Pro
            340                 345                 350

Ser Tyr Thr Ser Pro Asn Pro Asn Tyr Asp Glu Lys His Tyr Ile Glu
            355                 360                 365

Ala Phe Ser Pro Leu Leu Asn Ser Ala Gly Phe Pro Ala Arg Phe Ile
    370                 375                 380

Val Asp Thr Gly Arg Asn Gly Lys Gln Pro Thr Gly Gln Gln Gln Trp
385                 390                 395                 400

Gly Asp Trp Cys Asn Val Lys Gly Thr Gly Phe Gly Val Arg Pro Thr
                405                 410                 415

Ala Asn Thr Gly His Glu Leu Val Asp Ala Phe Val Trp Val Lys Pro
            420                 425                 430

Gly Gly Glu Ser Asp Gly Thr Ser Asp Thr Ser Ala Ala Arg Tyr Asp
    435                 440                 445

Tyr His Cys Gly Leu Ser Asp Ala Leu Gln Pro Ala Pro Glu Ala Gly
    450                 455                 460

Gln Trp Phe Gln Ala Tyr Phe Glu Gln Leu Leu Thr Asn Ala Asn Pro
465                 470                 475                 480

Pro Phe

<210> SEQ ID NO 2
<211> LENGTH: 512
<212> TYPE: PRT
<213> ORGANISM: Marinobacter algicola

<400> SEQUENCE: 2

```
Met Ala Thr Gln Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe
            20                  25                  30

Leu Gly Lys Val Val Leu Glu Lys Leu Ile Arg Thr Val Pro Asp Ile
        35                  40                  45

Gly Gly Ile His Leu Leu Arg Gly Asn Lys Arg His Pro Ala Ala
    50                  55                  60

Arg Glu Arg Phe Leu Asn Glu Ile Ala Ser Ser Val Phe Glu Arg
65              70                  75                  80

Leu Arg His Asp Asp Asn Glu Ala Phe Glu Thr Phe Leu Glu Arg
                85                  90                  95

Val His Cys Ile Thr Gly Glu Val Thr Glu Ser Arg Phe Gly Leu Thr
            100                 105                 110

Pro Glu Arg Phe Arg Ala Leu Ala Gly Gln Val Asp Ala Phe Ile Asn
            115                 120                 125

Ser Ala Ala Ser Val Asn Phe Arg Glu Glu Leu Asp Lys Ala Leu Lys
130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                165                 170                 175

Asn Ser Gly Gln Ile Thr Glu Ser Val Ile Lys Pro Ala Gly Glu Ser
            180                 185                 190

Ile Pro Arg Ser Thr Asp Gly Tyr Tyr Glu Ile Glu Glu Leu Val His
        195                 200                 205

Leu Leu Gln Asp Lys Ile Ser Asp Val Lys Ala Arg Tyr Ser Gly Lys
210                 215                 220

Val Leu Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
                245                 250                 255

Leu Leu Met Lys Ala Leu Ser Gly Arg Ser Leu Thr Ile Val Arg Pro
            260                 265                 270

Ser Ile Ile Glu Ser Ala Leu Glu Glu Pro Ser Pro Gly Trp Ile Glu
        275                 280                 285

Gly Val Lys Val Ala Asp Ala Ile Ile Leu Ala Tyr Ala Arg Glu Lys
290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                325                 330                 335

Ser Gly Ser Gly Gln Arg Ile Tyr Gln Cys Cys Ser Gly Gly Ser
            340                 345                 350

Asn Pro Ile Ser Leu Gly Lys Phe Ile Asp Tyr Leu Met Ala Glu Ala
        355                 360                 365

Lys Thr Asn Tyr Ala Ala Tyr Asp Gln Leu Phe Tyr Arg Arg Pro Thr
            370                 375                 380

Lys Pro Phe Val Ala Val Asn Arg Lys Leu Phe Asp Val Val Val Gly
385                 390                 395                 400

Gly Met Arg Val Pro Leu Ser Ile Ala Gly Lys Ala Met Arg Leu Ala
```

```
                405                 410                 415
Gly Gln Asn Arg Glu Leu Lys Val Leu Lys Asn Leu Asp Thr Thr Arg
            420                 425                 430

Ser Leu Ala Thr Ile Phe Gly Phe Tyr Thr Ala Pro Asp Tyr Ile Phe
            435                 440                 445

Arg Asn Asp Ser Leu Met Ala Leu Ala Ser Arg Met Gly Glu Leu Asp
        450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
                485                 490                 495

Arg Lys Leu Tyr Ser Leu Arg Ala Ala Asp Thr Arg Lys Lys Ala Ala
            500                 505                 510

<210> SEQ ID NO 3
<211> LENGTH: 465
<212> TYPE: PRT
<213> ORGANISM: Myceliophthora thermophilia

<400> SEQUENCE: 3

Ala Pro Val Ile Glu Glu Arg Gln Asn Cys Gly Ala Val Trp Thr Gln
1               5                   10                  15

Cys Gly Gly Asn Gly Trp Gln Gly Pro Thr Cys Cys Ala Ser Gly Ser
            20                  25                  30

Thr Cys Val Ala Gln Asn Glu Trp Tyr Ser Gln Cys Leu Pro Asn Ser
        35                  40                  45

Gln Val Thr Ser Ser Thr Thr Pro Ser Ser Thr Ser Thr Ser Gln Arg
    50                  55                  60

Ser Thr Ser Thr Ser Ser Ser Thr Thr Arg Ser Gly Ser Ser Ser Ser
65                  70                  75                  80

Ser Ser Thr Thr Pro Pro Val Ser Ser Pro Val Thr Ser Ile Pro
                85                  90                  95

Gly Gly Ala Thr Ser Thr Ala Ser Tyr Ser Gly Asn Pro Phe Ser Gly
            100                 105                 110

Val Arg Leu Phe Ala Asn Asp Tyr Tyr Arg Ser Glu Val His Asn Leu
        115                 120                 125

Ala Ile Pro Ser Met Thr Gly Thr Leu Ala Ala Lys Ala Ser Ala Val
    130                 135                 140

Ala Glu Val Pro Ser Phe Gln Trp Leu Asp Arg Asn Val Thr Ile Asp
145                 150                 155                 160

Thr Leu Met Val Gln Thr Leu Ser Gln Val Arg Ala Leu Asn Lys Ala
                165                 170                 175

Gly Ala Asn Pro Pro Tyr Ala Ala Gln Leu Val Val Tyr Asp Leu Pro
            180                 185                 190

Asp Arg Asp Cys Ala Ala Ala Ala Ser Asn Gly Glu Phe Ser Ile Ala
        195                 200                 205

Asn Gly Gly Ala Ala Asn Tyr Arg Ser Tyr Ile Asp Ala Ile Arg Lys
    210                 215                 220

His Ile Ile Glu Tyr Ser Asp Ile Arg Ile Ile Leu Val Ile Glu Pro
225                 230                 235                 240

Asp Ser Met Ala Asn Met Val Thr Asn Met Asn Val Ala Lys Cys Ser
                245                 250                 255

Asn Ala Ala Ser Thr Tyr His Glu Leu Thr Val Tyr Ala Leu Lys Gln
            260                 265                 270
```

-continued

```
Leu Asn Leu Pro Asn Val Ala Met Tyr Leu Asp Ala Gly His Ala Gly
        275                 280                 285
Trp Leu Gly Trp Pro Ala Asn Ile Gln Pro Ala Ala Glu Leu Phe Ala
    290                 295                 300
Gly Ile Tyr Asn Asp Ala Gly Lys Pro Ala Ala Val Arg Gly Leu Ala
305                 310                 315                 320
Thr Asn Val Ala Asn Tyr Asn Ala Trp Ser Ile Ala Ser Ala Pro Ser
                325                 330                 335
Tyr Thr Ser Pro Asn Pro Asn Tyr Asp Glu Lys His Tyr Ile Glu Ala
            340                 345                 350
Phe Ser Pro Leu Leu Asn Ser Ala Gly Phe Pro Ala Arg Phe Ile Val
            355                 360                 365
Asp Thr Gly Arg Asn Gly Lys Gln Pro Thr Gly Gln Gln Gln Trp Gly
        370                 375                 380
Asp Trp Cys Asn Val Lys Gly Thr Gly Phe Gly Val Arg Pro Thr Ala
385                 390                 395                 400
Asn Thr Gly His Glu Leu Val Asp Ala Phe Val Trp Val Lys Pro Gly
                405                 410                 415
Gly Glu Ser Asp Gly Thr Ser Asp Thr Ser Ala Ala Arg Tyr Asp Tyr
            420                 425                 430
His Cys Gly Leu Ser Asp Ala Leu Gln Pro Ala Pro Glu Ala Gly Gln
        435                 440                 445
Trp Phe Gln Ala Tyr Phe Glu Gln Leu Leu Thr Asn Ala Asn Pro Pro
        450                 455                 460
Phe
465
```